US011166907B2

(12) United States Patent
Zhang et al.

(10) Patent No.: US 11,166,907 B2
(45) Date of Patent: Nov. 9, 2021

(54) NON-COVALENTLY ASSEMBLED CONDUCTIVE HYDROGEL

(71) Applicant: DENOVOMATRIX GMBH, Dresden (DE)

(72) Inventors: Yixin Zhang, Dresden (DE); Yong Xu, Dresden (DE); Alvin Thomas, Dresden (DE)

(73) Assignee: DENOVOMATRIX GMBH, Dresden (DE)

(*) Notice: Subject to any disclaimer, the term of this patent is extended or adjusted under 35 U.S.C. 154(b) by 0 days.

(21) Appl. No.: 16/608,875

(22) PCT Filed: Apr. 27, 2018

(86) PCT No.: PCT/EP2018/060921
§ 371 (c)(1),
(2) Date: Oct. 28, 2019

(87) PCT Pub. No.: WO2018/197688
PCT Pub. Date: Nov. 1, 2018

(65) Prior Publication Data
US 2020/0188294 A1 Jun. 18, 2020

(30) Foreign Application Priority Data

Apr. 28, 2017 (EP) ..................... 17168824

(51) Int. Cl.
| | | |
|---|---|---|
| *A61K 9/00* | (2006.01) | |
| *A61K 47/58* | (2017.01) | |
| *A61K 47/54* | (2017.01) | |
| *A61K 9/06* | (2006.01) | |
| *A61K 47/10* | (2017.01) | |
| *A61K 35/33* | (2015.01) | |
| *A61K 35/35* | (2015.01) | |
| *A61K 35/44* | (2015.01) | |
| *A61K 35/51* | (2015.01) | |
| *A61K 47/40* | (2006.01) | |

(52) U.S. Cl.
CPC .............. *A61K 9/0009* (2013.01); *A61K 9/06* (2013.01); *A61K 35/33* (2013.01); *A61K 35/35* (2013.01); *A61K 35/44* (2013.01); *A61K 35/51* (2013.01); *A61K 47/10* (2013.01); *A61K 47/40* (2013.01); *A61K 47/542* (2017.08); *A61K 47/58* (2017.08)

(58) Field of Classification Search
None
See application file for complete search history.

(56) References Cited

U.S. PATENT DOCUMENTS

| | | | |
|---|---|---|---|
| 2006/0188486 A1* | 8/2006 | Carpenter | ............... A61L 15/26 424/93.7 |
| 2011/0200530 A1* | 8/2011 | Allemann | ............... A61K 39/44 424/9.1 |
| 2013/0177980 A1 | 7/2013 | Varghese et al. | |
| 2013/0296177 A1* | 11/2013 | Koepsel | ............... G01N 33/553 506/9 |
| 2015/0246132 A1* | 9/2015 | Wieduwild | .......... A61K 31/727 424/484 |

OTHER PUBLICATIONS

Sirivisoot et al. Interface Focus 2013 4:20130050, pp. 1-12 (Year: 2013).*
Freudenberg et al. Biomaterials 2009 30:5049-5060 (Year: 2009).*
Warren et al. Materials Research Society Symposium Proceedings 2013 1569:219-223 (Year: 2013).*

* cited by examiner

*Primary Examiner* — Robert A Wax
*Assistant Examiner* — Caralynne E Helm
(74) *Attorney, Agent, or Firm* — JMB Davis Ben-David

(57) ABSTRACT

The present invention provides a conductive hydrogel comprising a polystyrene sulfonate compound selected from poly(3,4-ethylenedioxythiophene) polystyrene sulfonate (PEDOT:PSS), reduced graphene oxide polystyrene sulfonate (rGO:PSS) and rGO:PEDOT:PSS; and a conjugate of polyethylene glycol (PEG) and a linker-(BX)n oligopeptide of formula (I)

PEG-linker-(BX)n    (I)

wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20. The invention further relates to processes for assembling the conductive hydrogel. The conductive hydrogel can be used in various biomedical applications, such as neuroprostheses, biosensors, nerve grafts, cell culture and encapsulation of cells and microorganisms as well as for drug delivery.

13 Claims, 26 Drawing Sheets
Specification includes a Sequence Listing.

Fig. 1B
|  | KA7 | KA5 | KA3 | KS7 | KG7 | RA7 | RG7 | KA7-RGDSP | NH$_2$ | Mal |
|---|---|---|---|---|---|---|---|---|---|---|
| starPEG | + x | + ✓ | + ✓ | n.t. | + x | + x | n.t. | n.t. | - | - |
| PEG-5k | + ✓ | + ✓ | + ✓ | + ✓ | + ✓ | + ✓ | + ✓ | + ✓ | - | - |
| PEG-10k | + ✓ | n.t. | n.t. | n.t. | n.t. | n.t. | n.t. | + ✓ | - | - |
| PEG-20k | + ✓ | n.t. | n.t. | n.t. | n.t. | n.t. | n.t. | + ✓ | - | - |
+: form hydrogel; -: do not form hydrogel;
✓: coherent hydrogel; x: non-homogenous hydrogel; n.t. not tested
Fig. 2A
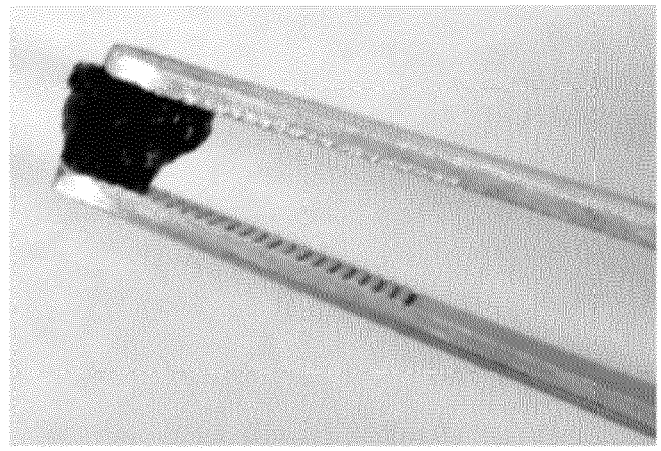
Fig. 2B
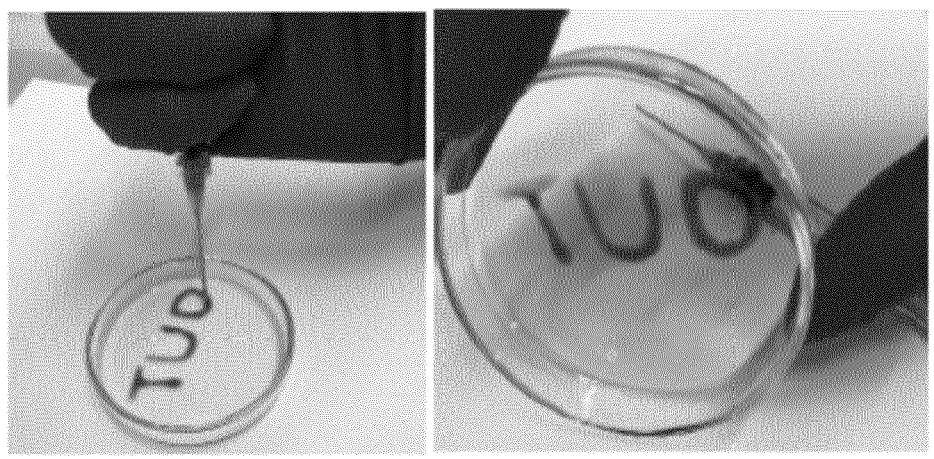

■ 500 µM 5KD-PEG-KA7 + 1% PEDOT:PSS
● 500 µM 5KD-PEG-KA5 + 1% PEDOT:PSS
▲ 500 µM 5KD-PEG-KA3 + 1% PEDOT:PSS

■ 500 µM 5KD-PEG-KA7 + 1% PEDOT:PSS
● 500 µM 10KD-PEG-KA7 + 1% PEDOT:PSS
▲ 500 µM 20KD-PEG-KA7 + 1% PEDOT:PSS

□ 500 µM 5KD-PEG-KA7 + 1% PEDOT:PSS
◇ 500 µM 5KD-PEG-KA7 + 1% PEDOT:PSS
△ 2.5 mM 5KD-PEG-KA7 + 1% PEDOT:PSS
▽ 2.5 mM 5KD-PEG-KA7 + 2% PEDOT:PSS

Actin Dapi

Hydrogel Actin Dapi

| | Solubility | Conductivity | Negative charges | Gelation with KA7-starPEG |
|---|---|---|---|---|
| Graphene | --- | +++ | - | - |
| Graphene oxide (GO) | +++ | + | + | - |
| rGO/PEDOT:PSS | ++ | ++ | +++ | + |
| rGO/PSS | +++ | ++ | +++ | + | a. $NH_2NH_2 \cdot H_2O$, PEDOT:PSS, 100 °C, 1h; b. $NH_2NH_2 \cdot H_2O$, PSS, 100 °C, 1h

SEQUENCE LISTING

```
<160> NUMBER OF SEQ ID NOS: 25

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Lys Ala Lys Ala Lys Ala Lys Ala Lys Ala
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2
```

Lys Ala Lys Ala Lys Ala Lys Ala Lys Ala Lys Ala
1               5                   10

<210> SEQ ID NO 3
<211> LENGTH: 14
<212> TYPE: PRT
<213> ORGANISM: Artificial sequence
<220> FEATURE:
<223> OTHER INFORMATION: Synthetic peptide

<400> SEQUENCE: 3

Lys Ala Lys Ala Lys Ala Lys Ala Lys Ala Lys Ala Lys Ala
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Lys Ser Lys Ser Lys Ser Lys Ser Lys Ser
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic peptide

<400> SEQUENCE: 5

Lys Ser Lys Ser Lys Ser Lys Ser Lys Ser Lys Ser
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic peptide

<400> SEQUENCE: 6

Lys Ser Lys Ser Lys Ser Lys Ser Lys Ser Lys Ser Lys Ser
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Arg Ala Arg Ala Arg Ala Arg Ala Arg Ala
1               5                   10

<210> SEQ ID NO 8
<211> LENGTH: 12
<212> TYPE: PRT
<213> ORGANISM: Artificial sequence
<220> FEATURE:
<223> OTHER INFORMATION: Synthetic peptide

<400> SEQUENCE: 8

Arg Ala Arg Ala Arg Ala Arg Ala Arg Ala Arg Ala

```
1               5                   10
```

<210> SEQ ID NO 9
<211> LENGTH: 14
<212> TYPE: PRT
<213> ORGANISM: Artificial sequence
<220> FEATURE:
<223> OTHER INFORMATION: Synthetic peptide

<400> SEQUENCE: 9

```
Arg Ala Arg Ala Arg Ala Arg Ala Arg Ala Arg Ala Arg Ala
1               5                   10
```

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

```
Arg Ser Arg Ser Arg Ser Arg Ser Arg Ser
1               5                   10
```

<210> SEQ ID NO 11
<211> LENGTH: 12
<212> TYPE: PRT
<213> ORGANISM: Artificial sequence
<220> FEATURE:
<223> OTHER INFORMATION: Synthetic peptide

<400> SEQUENCE: 11

```
Arg Ser Arg Ser Arg Ser Arg Ser Arg Ser Arg Ser
1               5                   10
```

<210> SEQ ID NO 12
<211> LENGTH: 14
<212> TYPE: PRT
<213> ORGANISM: Artificial sequence
<220> FEATURE:
<223> OTHER INFORMATION: Synthetic peptide

<400> SEQUENCE: 12

```
Arg Ser Arg Ser Arg Ser Arg Ser Arg Ser Arg Ser Arg Ser
1               5                   10
```

<210> SEQ ID NO 13
<211> LENGTH: 4
<212> TYPE: PRT
<213> ORGANISM: Artificial sequence
<220> FEATURE:
<223> OTHER INFORMATION: Synthetic peptide

<400> SEQUENCE: 13

```
Cys Trp Gly Gly
1
```

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

```
Cys Trp Gly Gly Arg Gly Asp Ser Pro
1               5
```

```
<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

Cys Trp Gly Gly Ile Lys Val Ala Val
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic peptide

<400> SEQUENCE: 16

Cys Trp Gly Gly Tyr Ile Gly Ser Arg
1               5

<210> SEQ ID NO 17
<211> LENGTH: 11
<212> TYPE: PRT
<213> ORGANISM: Artificial peptide
<220> FEATURE:
<223> OTHER INFORMATION: Synthetic peptide

<400> SEQUENCE: 17

Cys Trp Gly Gly Phe Arg Leu Val Phe Arg Tyr
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic peptide

<400> SEQUENCE: 18

Cys Trp Gly Gly Glu Ile Lys Leu Leu Ile Ser
1               5                   10

<210> SEQ ID NO 19
<211> LENGTH: 9
<212> TYPE: PRT
<213> ORGANISM: Artificial sequence
<220> FEATURE:
<223> OTHER INFORMATION: Synthetic peptide

<400> SEQUENCE: 19

Cys Trp Gly Gly His Ala Val Asp Ile
1               5

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Cys Trp Gly Gly Pro Gln Gly Ile Trp Gly Gln Gly Gly
1               5                   10
```

```
<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

Cys Trp Gly Gly Pro Val Gly Leu Ile Gly Gly Gly
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide

<400> SEQUENCE: 22

Cys Trp Gly Gly Val Pro Leu Ser Leu Tyr Ser Gly Gly Gly
1               5                   10

<210> SEQ ID NO 23
<211> LENGTH: 3
<212> TYPE: PRT
<213> ORGANISM: Artificial sequence
<220> FEATURE:
<223> OTHER INFORMATION: Synthetic peptide

<400> SEQUENCE: 23

Arg Gly Asp
1

<210> SEQ ID NO 24
<211> LENGTH: 4
<212> TYPE: PRT
<213> ORGANISM: Artificial sequence
<220> FEATURE:
<223> OTHER INFORMATION: Synthetic peptide

<400> SEQUENCE: 24

Arg Gly Asp Ser
1

<210> SEQ ID NO 25
<211> LENGTH: 5
<212> TYPE: PRT
<213> ORGANISM: Artificial sequence
<220> FEATURE:
<223> OTHER INFORMATION: Synthetic peptide

<400> SEQUENCE: 25

Arg Gly Asp Ser Pro
1               5
```

NON-COVALENTLY ASSEMBLED CONDUCTIVE HYDROGEL

CROSS-REFERENCE TO RELATED APPLICATIONS

This is the U.S. National Stage of International Patent Application No. PCT/EP2018/060921 filed Apr. 27, 2018, which claims priority to European Patent Application No. 17168824.5 filed on Apr. 28, 2017.

BRIEF DESCRIPTION OF THE DESCRIBED SEQUENCES

The amino acid sequences provided herewith are shown using standard three letter code for amino acids, as defined in 37 C.F.R. 1.822. The Sequence Listing is submitted as an ASCII text file which is incorporated by reference herein.

FIELD OF THE INVENTION

The present invention provides a conductive hydrogel comprising a polystyrene sulfonate compound selected from poly(3,4-ethylenedioxythiophene) polystyrene sulfonate (PEDOT:PSS), reduced graphene oxide polystyrene sulfonate (rGO:PSS) and rGO:PEDOT:PSS; and a conjugate of polyethylene glycol (PEG) and a linker-(BX)n oligopeptide of formula (I)

$$\text{PEG-linker-(BX)}_n \quad (I)$$

wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20. The invention further relates to processes for assembling the conductive hydrogel. The conductive hydrogel mimics the extracellular matrix and can be used in various biomedical applications, such as neuroprostheses, biosensors, nerve grafts, cell culture and encapsulation of cells, organoids, and microorganisms as well as for drug delivery.

BACKGROUND ART

Conductive biopolymers have great potentials across a wide range of biomedical applications, including neuroprostheses, biosensors, nerve grafts and drug delivery. One of the major challenges restricting optimal bio-integration is the substantial mismatch between electronic components and native tissues. The development of conductive polymers to mimic the extracellular matrix (ECM) aims to combine the biochemical and viscoelastic features of native tissue with electronic properties, resulting in seamless electronic-biological interface. A non-covalently assembled network using modular building blocks is of great interest, as it can lead to generalizable platforms with tunable mechanophysical, electrochemical and biochemical properties. Moreover, the network dynamics associated with reversible non-covalent interactions is important for many biomedical applications, such as chemical reaction-free cell encapsulation, injection, and self-healing.

To reduce the complexity of ECM to a non-covalently assembled matrix with modular and chemically defined components, there was a previously developed a physical hydrogel system based on the interaction between peptide motif (BA)n (where B is lysine or arginine and A is alanine) and negatively charged oligosaccharides. Through varying the peptide and sulfated oligosaccharide (e.g. dextran sulfate, heparin) components, the biomaterials could be tailored for applications such as 3D cell culture and drug release (WO2014040591 A2). This dynamic network showed shear-thinning and self-healing properties, which are essential for injectability. Injected hydrogels in mice have shown high biocompatibility and did not cause adverse inflammatory response.

WO 2008/124165 A2 discloses non-covalent, self-organizing hydrogels, which are produced by coupling a dipeptide motif to a polymer chain.

Further known are low-molecular-weight heparin and a peptide bound to star PEG. A hydrogel is formed by the non-covalent bond between the peptide and heparin. The peptide, derived from HIP, contains the sequence (KA)4 (Nori Yamaguchi et al: "Rheological Characterization of Polysaccharide-Poly(ethylene glycol) Star Copolymer Hydrogels", BIOMACROMOLECULES, Vol. 6, No. 4, 28 May 2005 (2005 May 28), pages 1931-1940; Nori Yamaguchi et al: "Polysaccharide poly(ethylene glycol) star copolymer as a scaffold for the production of bioactive hydrogels", BIOMACROMOLECULES, Vol. 6, No. 4, July 2005 (2005 July), pages 1921-1930.

Generally, the formation of hydrogels which consist of a conjugate of starPEG with a heparin binding peptide and low-molecular-weight heparin is already known from U.S. Pat. No. 6,958,212 B1; Kyung Jae Jeong et al: "Interplay between Covalent and Physical Interactions within Environment Sensitive Hydrogels", BIOMACROMOLECULES, Vol. 10, No. 5, 23 Mar. 2009 (2009 Mar. 23), pages 1090-1099; Mikhail V. T et al: "Enzymatically degradable heparin-polyethylene glycol gels with controlled mechanical properties", CHEMICAL COMMUNICATIONS, Vol. 46, No. 7, 16 Dec. 2009 (2009 Dec. 16), pages 1141-1143; Mikhail V. Tsurkan et al: "Modular StarPEG-Heparin-Gels with Bifunctional Peptide Linkers", MACROMOLECULAR RAPID COMMUNICATIONS, Vol. 31, No. 17, 16 Aug. 2010 (2010 Aug. 16), pages 1529-1533; Seal B. L. et al: "Physical matrices stabilized by enzymatically sensitive covalent crosslinks", ACTA BIOMATERIALIA, Vol. 2, No. 3, 1 May 2006 (2006 May 1), pages 241-251; Alison B. Pratt et al: "Synthetic extracellular matrices for in situ tissue engineering", BIOTECHNOLOGY AND BIOENGINEERING, Vol. 86, No. 1, 12 Feb. 2004 (2004 Feb. 12), pages 27-36; Brandon I. Seal et al: "Physical Polymer Matrices Based on Affinity Interactions between Peptides and Polysaccharides", BIOMACROMOLECULES, Vol. 4, No. 6, 1 Nov. 2003 (2003 Nov. 1), pages 1572-1582; Freudenberg U. et al: "A star-PEG-heparin hydrogel platform to aid cell replacement therapies for neurodegenerative diseases", BIOMATERIALS, Vol. 30, No. 28, October 2009 (2009 October), pages 5049-5060; Nie T. et al: "Production of heparin containing hydrogels for modulating cell responses", ACTA BIOMATERIALIA, Vol. 5, No. 3, March 2009 (2009 March), pages 865-875; Benoit et al: "The effect of heparin-functionalized PEG hydrogels on three-dimensional human mesenchymal stem cell osteogenic differentiation", BIOMATERIALS, Vol. 28, No. 1, 1 Jan. 2007 (2007 Jan. 1), pages 66-77; Brandon L. Seal et al: "Viscoelastic Behavior of Environmentally Sensitive Biomimetic Polymer Matrices", MACROMOLECULES, Vol. 39, No. 6, 23 Feb. 2006 (2006 Feb. 23), pages 2268-2274.)

WO 2016/101044 A1 relates to electrically conductive polymeric material. The method for producing the same is very complex and requires the provision of a polymeric network having a short chain conductive polymer dispersed in the polymeric network and, in particular, a step of electropolymerising a conductive polymer within the polymeric network. Said short chain conductive polymer can e.g. be PEDOT:PSS. The conductive polymers can be comprised in poly(vinyl alcohol) methacrylate (PVA-MA) hydrogels. Moreover, conductive films comprising PEDOT:PSS and polyurethane are disclosed. The electrically conductive polymeric materials may be used as hydrogel electrode tracks or soft and flexible electroactive materials for neuroprosthetic devices.

U.S. Pat. No. 9,299,476 B2 relates to a conductive polymer homogeneously distributed, but not cross-linked, within a hydrogel for use with medical electrodes.

However, the conventional heparin-containing hydrogels discussed above are not conductive and are formed using branched starPEG. Whereas such a branched polymer can increase the crosslinking degree, linear PEGs are cheaper and possess a narrower molecular weight distribution. Moreover, it is much easier to separate a linear PEG chain with two peptides bound to it from that with only one peptide, as compared to purify the starPEG comprising 4 peptides from a mixture of star PEGs of lower degree of modification. However, using linear PEG resulted in very weak hydrogels with heparin. Therefore, based on the strength of interaction between anionic polymer and peptide, linear PEG and starPEG must be selected accordingly. Linear PEG can be used when the interaction is strong, thus less crosslinking degree would be required. Moreover, the conventional nonconductive and conductive hydrogels discussed above do not always mimic the extracellular matrix properly and have therefore drawbacks regarding their use in biomedical applications.

BRIEF DESCRIPTION OF THE INVENTION

To overcome the obstacles and disadvantages of conventional hydrogels, it is the object of the present invention to provide a hydrogel, which is conductive, stable and easy and cheap to produce.

This object is solved by providing a conductive hydrogel comprising
a polystyrene sulfonate compound selected from poly(3,4-ethylenedioxythiophene) polystyrene sulfonate (PEDOT:PSS), reduced graphene oxide polystyrene sulfonate (rGO:PSS) and rGO:PEDOT:PSS; and
a conjugate of polyethylene glycol (PEG) and a linker-(BX)n oligopeptide of formula (I):

PEG-linker-(BX)n     (I)

wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20.

In one embodiment of the invention, the conductive hydrogel does not contain sulfated oligosaccharides.

In an alternative embodiment, the conductive hydrogel comprises both, polystyrene sulfonate compound selected from poly(3,4-ethylenedioxythiophene) polystyrene sulfonate (PEDOT:PSS), reduced graphene oxide polystyrene sulfonate (rGO:PSS) and rGO:PEDOT:PSS, and a sulfated oligosaccharide.

In a further embodiment, the invention provides a conductive hydrogel which is assembled non-covalently.

In a further embodiment, the invention provides a conductive hydrogel which comprises a peptide sequence that functions as an attachment sequence for cells and biomolecules.

In a further embodiment, the invention provides a conductive hydrogel which is stable under acidic and alkaline conditions and against various solvents.

In a further embodiment, the invention provides a conductive hydrogel, which has advantageous properties such as self-healing and molecular ordering; tuneability of rheological properties and electrical impedance; injectability; and biocompatibility.

In a further embodiment, the invention provides a conductive hydrogel, which mimics the extracellular matrix properly and is thus advantageous in regard to its use in biomedical applications.

In a further embodiment, the invention provides a conductive hydrogel, which can form a conductive 3D matrix.

In a further embodiment, the invention provides a conductive hydrogel, which comprises cells, organoids, microorganisms or an active pharmaceutical ingredient.

The invention further relates to processes for preparing a conductive hydrogel according to the invention.

In a further embodiment, the invention relates to the use of the conductive hydrogel according to the invention in biomedical applications, such as neuroprostheses, biosensors, nerve grafts, cell culture and drug delivery.

BRIEF DESCRIPTION OF THE DRAWINGS

Specific embodiments of the present invention are described in the working examples with reference to the accompanying drawings.

Figure M-P shows the enhanced expression of surface marker Cardiac Troponin T upon applying electric stimulation to MSC encapsulated in the 5 kD-PEG-KA7/PEDOT:PSS hydrogel.

Figure 5A:
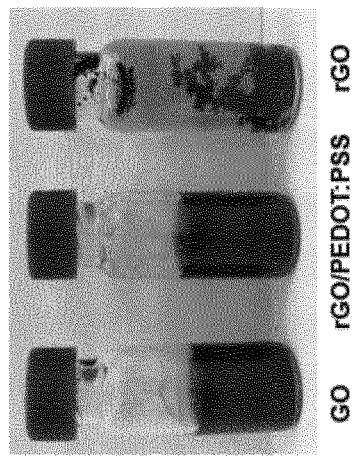

FIG. 5A shows that reducing GO in the present of PEDOT/PSS leads to rGO/PEDOT:PSS with retained water-solubility. Reducing GO in the present of PSS also led to water-soluble and conductive material rGO/PSS. Hydrogel can be formed by using rGO:PSS or rGO:PEDOT:PSS.

Figure 5B:
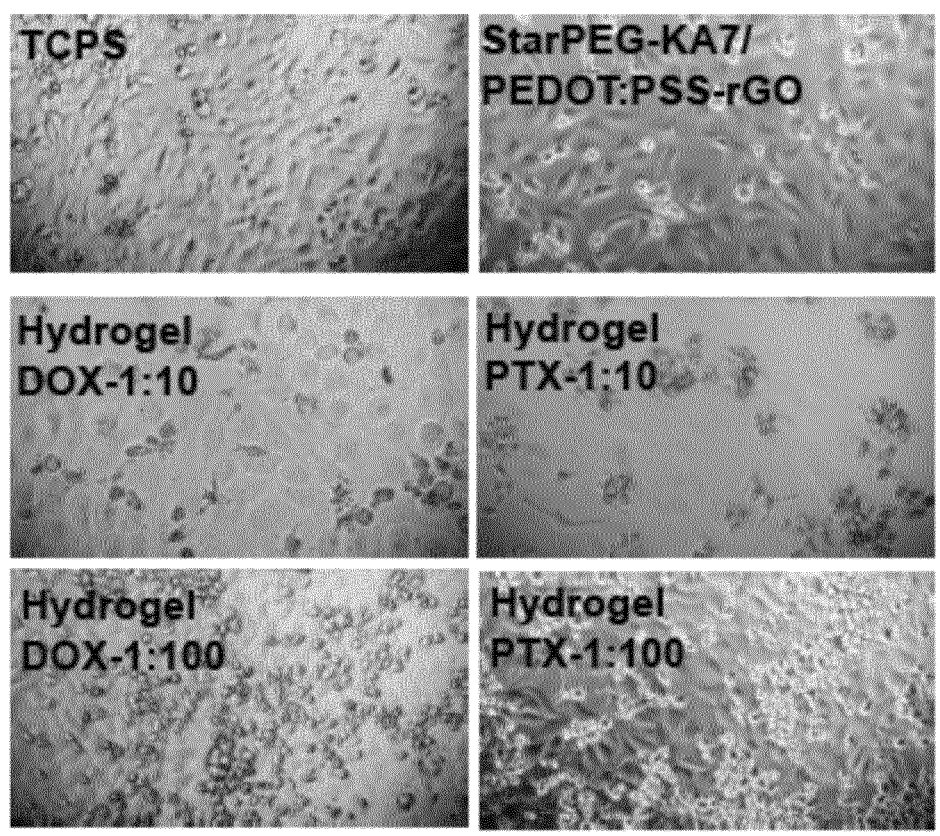

FIG. 5B shows the cytotoxic effect on HeLa cells after treating them with released drug from doxorubicin (DOX)- or paclitaxel (PTX)-encapsulating rGO:PEDOT:PSS/starPEG-KA7 hydrogels. The released compounds were diluted 10× or 100× times for the treatment.

Figure 5C:
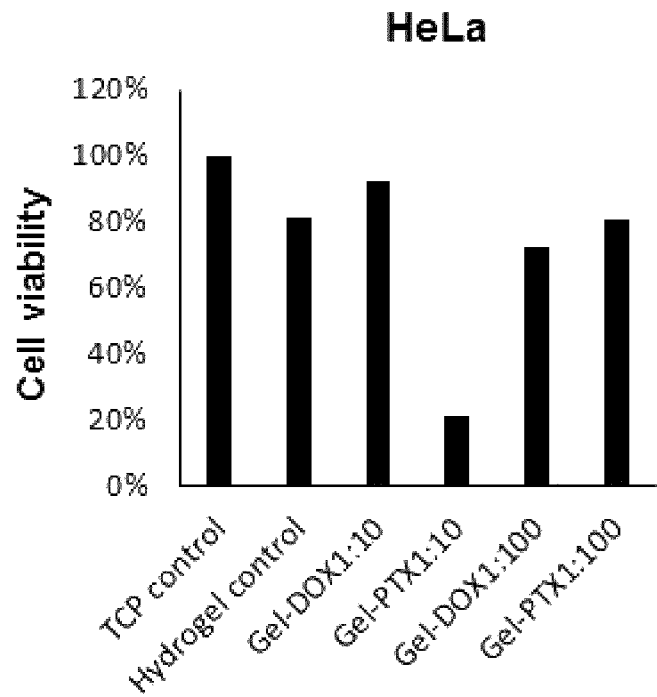

FIG. 5C shows the statistical analysis of the cytotoxic effect on HeLa cells after treating cells with released drug from doxorubicin (DOX)- or paclitaxel (PTX)-encapsulating hydrogels.

Figure 6A:
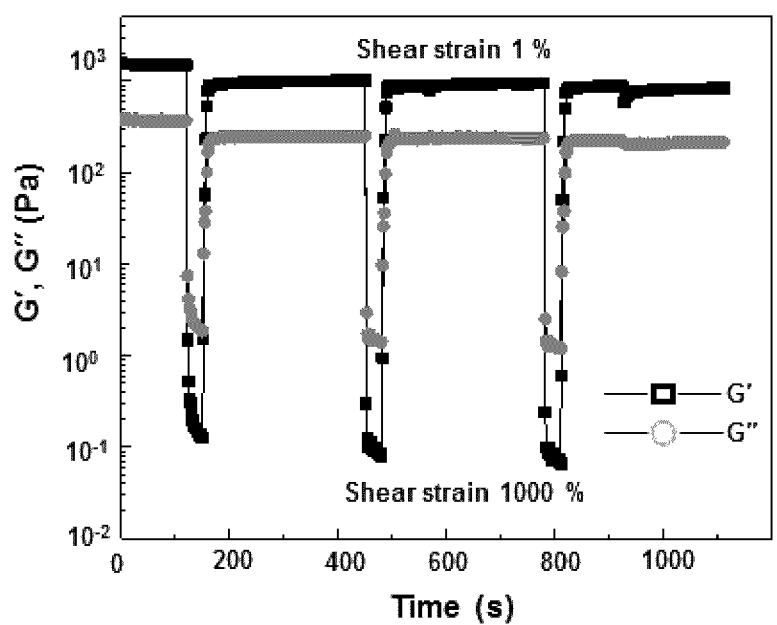

FIG. 6A shows the instant recovery of the rGO:PEDOT:PSS/starPEG-KA7 hydrogel characteristics (G'>>G") after a strong strain to break the hydrogel was applied.

Figure 6B:
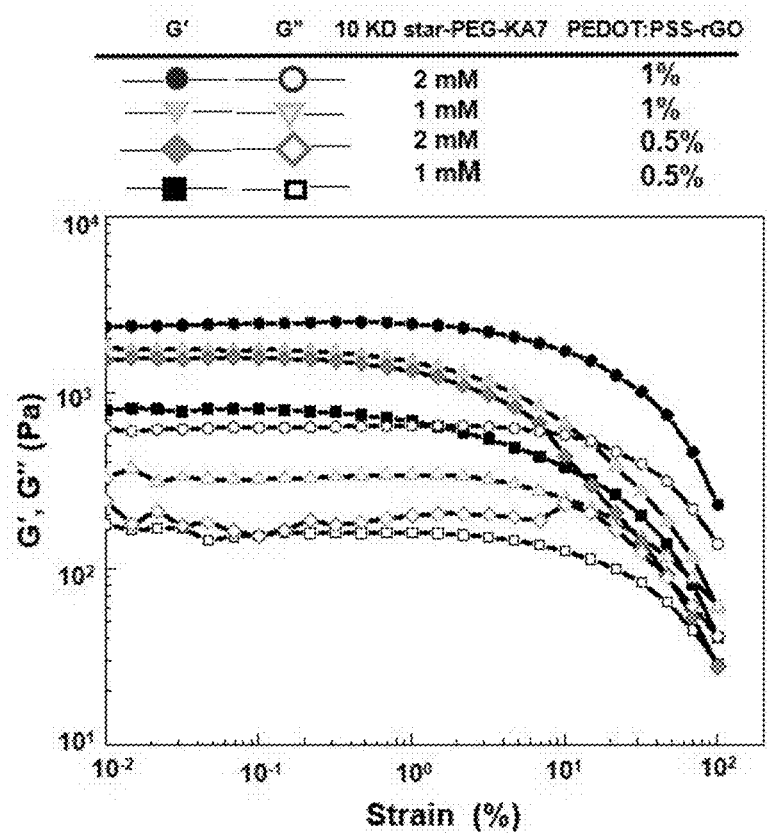

FIG. 6B shows that tuning the concentrations of rGO:PEDOT:PSS and starPEG-KA7 can change the rheology property of the resulting hydrogels. High concentrations of rGO:PEDOT:PSS and starPEG-KA7 lead to stiff hydrogels.

Figure 7A:
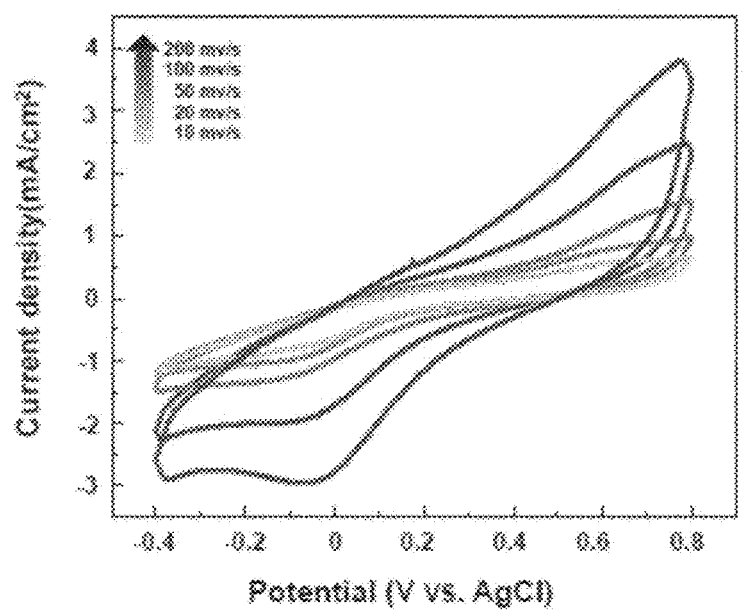

FIG. 7A shows a typical cyclic voltammetry (CV) curve of rGO:PEDOT:PSS/starPEG-KA7 hydrogel, showing the oxidation peak between +500 mV and +650 mV and reduction occurring between −100 mV and −50 mV.

Figure 7B:
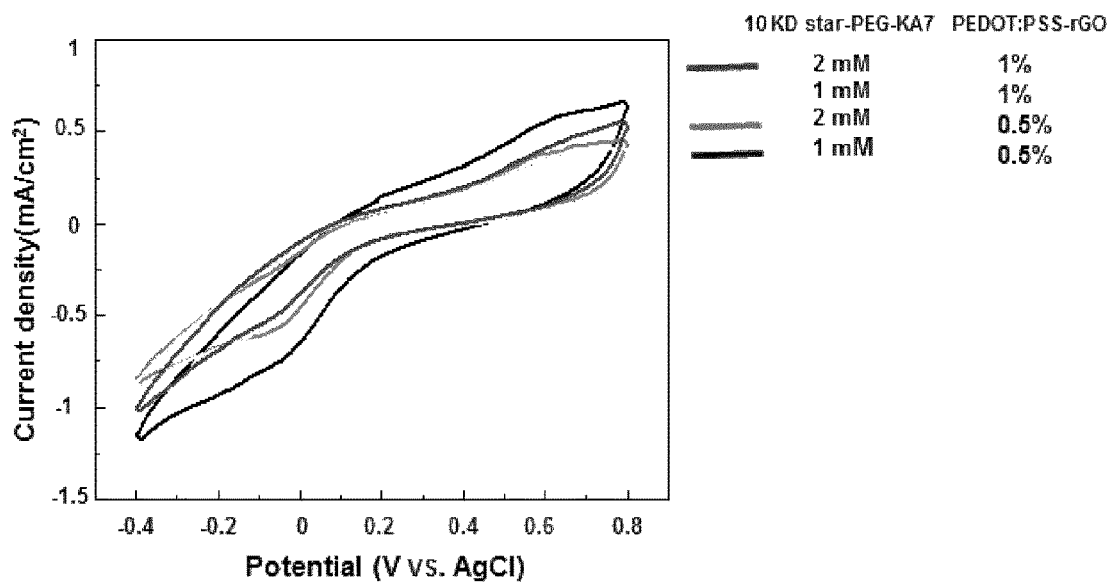
Figure 7C:
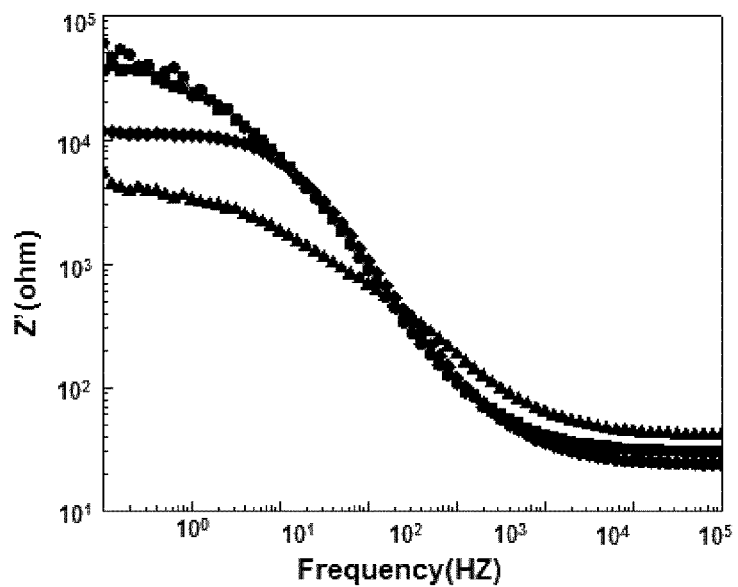
Figure 7D:
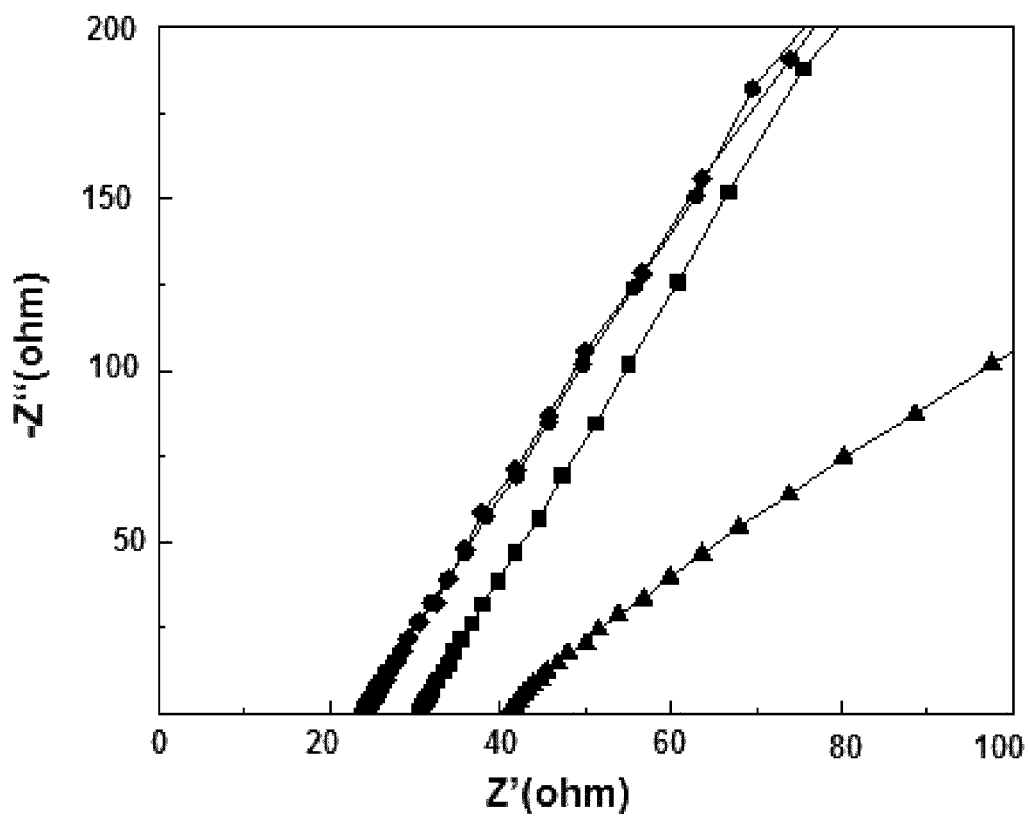

FIG. 7B-D shows that tuning the concentrations of rGO:PEDOT:PSS and starPEG-KA7 can change the electrochemical property of the resulting hydrogels.

Figure 8A:
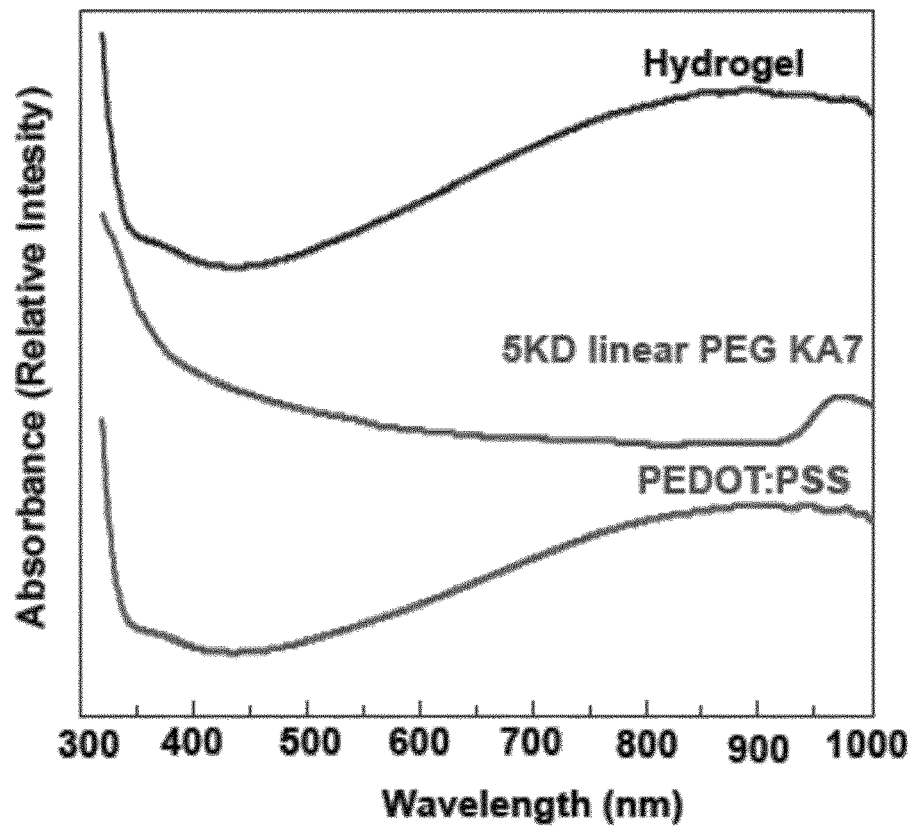

FIG. 8A shows PEDOT:PSS and rGO:PEDOT:PSS have the maximal absorption in the near IR region.

Figure 8B:
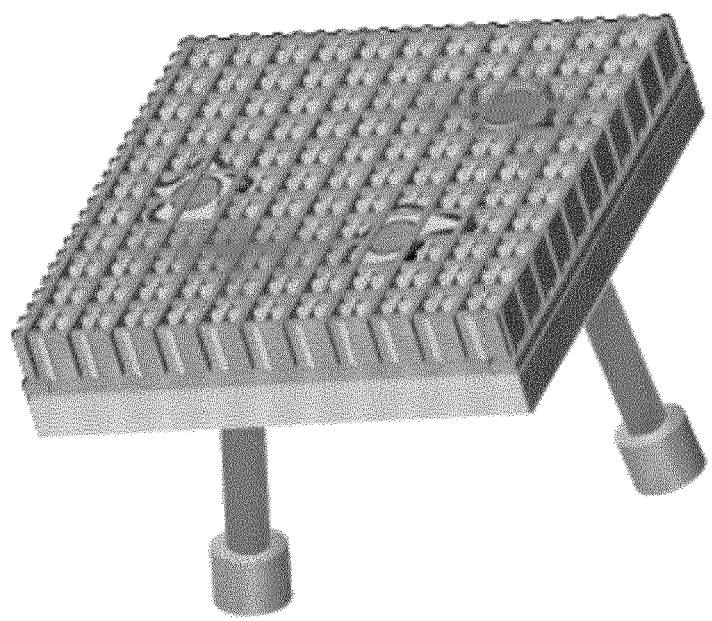

FIG. 8B shows the principle of using IR light to kill cells cite-specifically through the IR-absorbing property of conductive hydrogels.

Figure 8C:
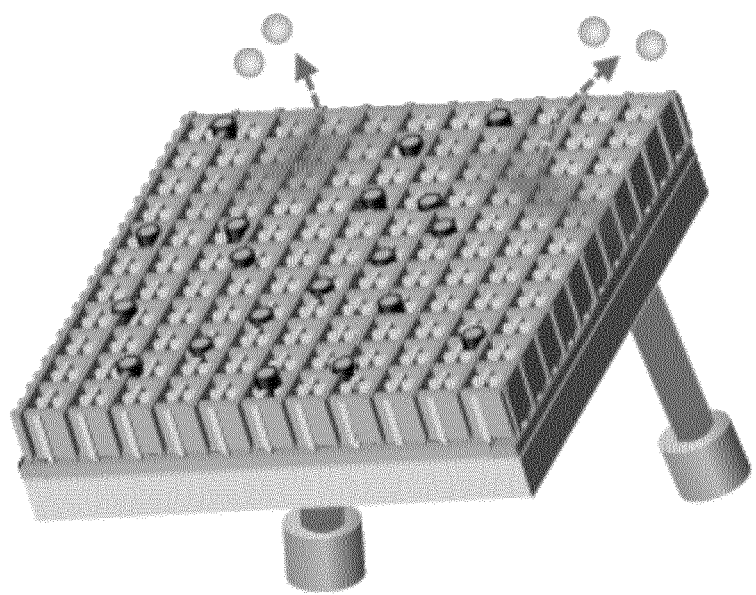

FIG. 8C shows the principle of using IR light for drug release cite-specifically through the IR-absorbing property of conductive hydrogels.

DETAILED DESCRIPTION OF THE INVENTION

The inventors have surprisingly found that polystyrene sulfonate containing compounds are suitable for producing conductive hydrogels which are capable of a non-covalent self-assembly, in which the polystyrene sulfonate compound is homogeneously distributed and cross-linked with the hydrogel matrix.

As those skilled in the art will appreciate, a conductive polymer requires a dopant (e.g. an ionically charged species) in order for the polymer to form highly conductive pathways and be capable of passing electronic or ionic charges. Such dopants are typically sulfonated molecules (e.g. p-toluene sulfonic acid, poly(styrene sulfonate), dodecyl benzene sulfonate), but can be other groups such as perchlorates, carbonates or amino acids.

According to the present invention, a dopant is preferably present in the polymeric network. The dopant may be immobilized within the polymeric network. For example, the dopant may form part of the polymer constituents of the polymeric network. Alternatively, the dopant may be bound to the conductive polymer which is assembled with the polymer constituents of the polymeric network.

In a more preferred embodiment, the dopant is part of the conductive polymer. For example, in PEDOT:PSS the sulfonate group of the PSS provides the dopant in the form of the sulfonate anion covalently bound to the phenyl group of the polystyrene. Other example are reduced graphene oxide polystyrene sulfonate (rGO:PSS) and rGO:PEDOT:PSS.

According to a most preferred embodiment, the invention specifically provides a conductive hydrogel which comprises a polystyrene sulfonate compound selected from poly(3,4-ethylenedioxythiophene) polystyrene sulfonate (PEDOT:PSS), reduced graphene oxide polystyrene sulfonate (rGO:PSS) and rGO:PEDOT:PSS.

As poly(3,4-ethylenedioxythiophene) polystyrene sulfonate (PEDOT:PSS) is a widely used conductive polymer, which is also highly negatively charged, it was incorporated into the non-covalently assembled hydrogel matrices of the invention, for generating conductive biomaterials. Moreover, it led to a tunable modular system possessing a structure-function relationship between the other matrix components, such as the oligopeptide, polymer linkage; and the mechanical, electronic and cell adhesive properties.

PEDOT:PSS or poly(3,4-ethylenedioxythiophene) polystyrene sulfonate is a polymer mixture of two ionomers. One component in this mixture is made up of sodium polystyrene sulfonate which is a sulfonated polystyrene. Part of the sulfonyl groups are deprotonated and carry a negative charge. The other component poly(3,4-ethylenedioxythiophene) or PEDOT is a conjugated polymer and carries positive charges and is based on polythiophene. Together the charged macromolecules form a macromolecular salt.

In the conductive hydrogel of the present invention, the conductive polymer PEDOT is no more than 10000 monomeric units in length. In some embodiments, the PEDOT is no more than 1000 monomeric units in length. In some embodiments, the PEDOT used in the method has from about 5 to about 1000 monomeric units. In some embodiments, the PEDOT comprises from about 5-800, 5-500, 5-100, 5-80, 5-50, 5-25, 5-10, 10-1000, 10-800, 10-500, 10-100, 10-80, 10-50, 10-25, 20-1000, 20-800, 20-500, 20-100, 20-80, or 20-50 monomeric units.

In a preferred embodiment, the PEDOT:PSS used to prepare the conductive hydrogel of the invention is commercially available, for example from SigmaAldrich.

In a further embodiment of the invention, conductive hydrogels comprising a graphene compound are provided. While graphene has very poor water solubility, graphene oxide (GO) was used to prepare the conductive hydrogels of the invention. GO possesses negatively charged carboxylic acid groups and is water-soluble, while electron mobility in the conjugate system is remarkably reduced. After incubation over night with an PEG-oligopeptide, no hydrogel formation could be observed. Apparently, the carboxylic acid presented on graphene was not sufficient to form stable crosslinking with positively charged peptide-polymer. But, reducing GO in the presence of PEDOT/PSS led to reduced GO (rGO) and to rGO/PEDOT:PSS with retained water-solubility, while the conductivity was remarkably enhanced, as compared with GO. Reducing GO in the presence of PSS also led to water-soluble and conductive material rGO/PSS.

In a most preferred embodiment, the conductive hydrogels of the invention comprise PEDOT:PSS. It was surprisingly found that PEDOT:PSS provides stronger interaction than heparin and dextran sulfate (DS) to assemble PEG and $(BX)_n$-oligopeptides to form non-covalent networks. A further advantage of using PEDOT:PSS in the hydrogels of the invention is that PEDOT:PSS containing hydrogels are very stable. No degradation could be observed after incubating the biomaterials in PBS buffer or cell culture medium over a period up to half a year. The hydrogels were also resistant to harsh conditions such as deionized water, DMF, DMSO, ethanol, 1 M HCl, and 1 M NaOH.

In a further most preferred embodiment, the conductive hydrogels of the invention comprise rGO:PEDOT:PSS.

In a further most preferred embodiment, the conductive hydrogels of the invention comprise rGO:PSS.

To form the conductive hydrogel according to the invention, a polymeric network is required into which the polystyrene sulfonate compound is incorporated.

Generally, the polymeric network may be any polymeric network. Preferably the polymeric network is capable of self-assembly. A polymeric network that is capable of self-assembly is easy to produce, guarantees the homogeneous distribution of the matrix building blocks and does not require additional steps for forming the conductive polymer, such as nucleation and electropolymerization.

In one embodiment, the polymeric network comprises an elastomer, such as a polyurethane elastomer or a silicone rubber elastomer.

In a preferred embodiment, the polymeric network is a hydrogel. In some embodiments, the hydrogel or elastomer may comprise two or more polymer constituents in order to take advantage of the properties that each of the polymer constituents impart to the resultant hydrogel or elastomer.

Non-limiting examples of polymers suitable for forming a hydrogel or elastomer to provide the polymeric network include polyvinyl alcohol (PVA), polyethylene glycol, poly (acrylic acid) and its derivatives; poly(ethyleneoxide) and its copolymers, polyphosphazene, silicones, polyacrylamides, polyvinylpyrrolidones, poly-hydroxyethylmethacrylate, polyurethanes and its derivatives; or combinations thereof.

In a more preferred embodiment, the polymer suitable for forming the conductive hydrogel of the invention is polyethylene glycol (PEG).

PEG is an oligomer or polymer composed of ethylene oxide monomers. Because different applications require different polymer chain lengths, PEGs are prepared by polymerization of ethylene oxide and are commercially available over a wide range of molecular weights from 300 g/mol to 10,000,000 g/mol. While PEGs with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete.

PEGs are also available with different geometries:

Linear PEGs, where the ethylene oxide monomers are bound to each other in an unbranched polymer chain;

Branched PEGs, which have three to ten PEG chains emanating from a central core group;

Star PEGs, which have 10 to 100 PEG chains emanating from a central core group; and Comb PEGs, which have multiple PEG chains normally grafted onto a polymer backbone.

The numbers that are often included in the names of PEGs indicate their average molecular weights (e.g. a PEG with n=9 would have an average molecular weight of approximately 400 daltons, and would be labeled PEG 400). Most PEGs include molecules with a distribution of molecular weights (i.e. they are polydisperse). The size distribution can be characterized statistically by its weight average molecular weight (Mw) and its number average molecular weight (Mn), the ratio of which is called the polydispersity index (Mw/Mn). MW and Mn can be measured by mass spectrometry.

PEG is soluble in water, methanol, ethanol, acetonitrile, benzene, and dichloromethane, and is insoluble in diethyl ether and hexane.

In a preferred embodiment, the conductive hydrogel of the invention comprises a starPEG. Suitably, said starPEG has a molecular weight in the range of 4 kD to 40 kD, preferably in the range of 4 kD to 30 kD, more preferably in the range of 4 kD to 20 kD, most preferably in the range of 4 kD to 10 kD. Further most preferably, said starPEG is a 4-arm starPEG. The use of 4-arm starPEG in the conductive hydrogels according to the invention has been found to be especially suitable, when the conductive hydrogel comprises a graphene compound, such as rGO:PSS or rGO:PEDOT:PSS as conductive polymer.

More preferably, the conductive hydrogel of the invention comprises a linear PEG. Using linear PEGs has the advantage that linear PEGs are cheaper and possess a narrower molecular weight distribution. Moreover, it is much easier to separate a linear PEG chain with two peptides bound to it from that with only one peptide, as compared to purify the 4-arm starPEG comprising 4 peptides from a mixture of star PEGs of lower degree of modification. The use of 4-arm starPEG in the conductive hydrogels according to the invention has been found to be especially suitable, when the conductive hydrogel comprises PEDOT:PSS as conductive polymer.

Most preferably, the linear PEG comprised in the conductive hydrogel according to the invention has a molecular weight in the range of 1 kD to 100 kD, preferably in the range 2 kD to 80 kD, 3 kD to 60 kD, 4 kD to 40 kD, most preferably in the range of 5 kD to 20 kD. Even most preferably, the linear PEG comprised in the conductive hydrogel according to the invention has a molecular weight selected from 5 kD, 10 kD, 15 kD and 20 kD.

In a further preferred embodiment, the PEG, which is used to prepare the conductive hydrogel of the invention, is functionalized. By "functionalize" is meant to modify a molecule in a manner that results in the attachment of a functional group or moiety. For example, a molecule may be functionalized by the introduction of a molecule which makes the molecule a strong nucleophile or a conjugated unsaturation. Preferably a molecule, for example PEG, is functionalized to become a thiol, amine, acrylate, azide, alkyne, or quinone. More preferably, for use in the preparation of the conductive hydrogel of the invention, the PEG is maleimide-functionalized, carboxylic acid-functionalized, amino-functionalized, azide-functionalized, or alkyne-functionalized. This type of functionalization is required to conjugate PEG to the oligopeptide of formula (I). Thus, in a most preferred embodiment, the starPEG, in particular the 4-arm PEG, and/or the linear PEG is functionalized with a maleimide, carboxylic acid or amino group.

It has been shown that the use of polymer-peptide-conjugates leads to the formation of hydrogels that exhibit self-organizing properties (WO 2014040591 A2). Accordingly, in a preferred embodiment, the conductive hydrogel of the invention comprises a conjugate of oligopeptides and polyethylene glycol (PEG), e.g. conjugates of 4-arm starPEG and oligopeptides or linear PEG and oligopeptides.

In a more preferred embodiment, the conductive hydrogel of the invention comprises a conjugate of PEG and a linker-(BX)n oligopeptide of formula (I)

PEG-linker-(BX)n    (I)

wherein B is lysine or arginine, X is selected from alanine, glycine, serine, threonine, tyrosine, glutamic acid or aspartic acid and n is an integer selected from 3, 4, 5, 6, 7, 8, 9, 10, 11, and 12.

The PEG-oligopeptide conjugate suitably comprises one, two or more of the oligopeptides which are coupled to a linear or 4-arm starPEG.

n is preferably an integer selected from 3, 4, 5, 6, 7, 8, 9, 10, 11, 12, 13, 14, 15, 16, 17, 18, 19 and 20.

More preferably, n is an integer selected from 5, 6, 7, 8 and 9.

Most preferably, n is 6 or 7.

In a preferred embodiment, B is lysine or arginine.

In a further preferred embodiment, X is alanine or serine.

In the peptides of the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

(BX)n is preferably selected from KA7, KA6, KA5, KS7, KS6, KS5, RA7, RA6, RA5, RS7, RS6, and RS5. Most preferably, (BX)n is selected from: KA7, KA6, KA5, KS7, KS6 and KS5. The respective peptide sequences are shown in table 1 below:

TABLE 1

Preferred peptide sequences of the (BX)n

| (BX)n Peptide | Sequence | SEQ ID NO. |
|---|---|---|
| KA5 | KAKAKAKAKA | 1 |
| KA6 | KAKAKAKAKAKA | 2 |
| KA7 | KAKAKAKAKAKAKA | 3 |
| KS5 | KSKSKSKSKS | 4 |
| KS6 | KSKSKSKSKSKS | 5 |
| KS7 | KSKSKSKSKSKSKS | 6 |
| RA5 | RARARARARA | 7 |
| RA6 | RARARARARARA | 8 |
| RA7 | RARARARARARARA | 9 |
| RS5 | RSRSRSRSRS | 10 |
| RS6 | RSRSRSRSRSRS | 11 |
| RS7 | RSRSRSRSRSRSRS | 12 |

The PEG-oligopeptide conjugate of the invention comprises in a further embodiment of the invention a linker. The linker is a peptide and has various functions: In one aspect of the invention, the linker is used to attach the (BX)n peptide to the PEG polymer. In another aspect, the linker can be used to improve the adhesion of cells to the conductive hydrogel of the invention resulting in the provision of a biopolymer. In still a further aspect of the invention, the linker can be used to facilitate the proteolysis of such a biopolymer by cells or proteases in vivo, e.g. in the case of targeted drug delivery using the conductive hydrogel of the invention. In a preferred embodiment, the linker sequence is selected from the group of sequences shown in the table 2 below:

TABLE 1

Preferred peptide sequences of the linker

| Linker-Peptide | Sequence | SEQ ID NO. |
|---|---|---|
| L1 | CWGG | 13 |
| L2 | CWGGRGDSP | 14 |
| L3 | CWGGIKVAV | 15 |
| L4 | CWGGYIGSR | 16 |
| L5 | CWGGFRLVFRY | 17 |
| L6 | CWGGEIKLLIS | 18 |
| L7 | CWGGHAVDI | 19 |
| L8 | CWGGPQGIWGQGG | 20 |
| L9 | CWGGPVGLIGGG | 21 |
| L10 | CWGGVPLSLYSGGG | 22 |

One special feature of the conductive hydrogel of the invention is that a variety of bioactive peptides can be incorporated into the resulting biomaterial structure. For example, a peptide as part of the linker can be designed to be a substrate for an enzyme used by cells migration through tissues and remodel tissues (e.g., as a substrate for plasmin, elastase or matrix metalloproteinases (MMPs), such as collagenase). The degradation characteristics of the gels can be manipulated by changing the sequence of the linker peptide. One may make a gel that is degradable by collagenase, but not plasmin, or by plasmin, but not collagenase. Furthermore, it is possible to make the gel degrade faster or slower in response to such an enzyme, simply by changing the amino acid sequence so as to alter the Km or kcat, or both, of the enzymatic reaction. One can thus make a biomaterial that is biomimetic, in that it is capable of being remodeled by the normal remodeling characteristics of cells.

Adhesion Sites

One can incorporate peptide ligands for cell adhesion, namely peptides that bind to adhesion-promoting receptors on the surfaces of cells into the biomaterials of the present invention. It is straightforward to incorporate a variety of such adhesion-promoting peptides, such as the RGD (SEQ ID NO: 23) sequence from fibronectin or the RGDS (SEQ ID NO: 24) sequence. The RGD peptide (SEQ ID NO: 23) is the binding motif of fibronectin to cell surface receptor integrin. The RGDS sequence (SEQ ID NO: 24) was found initially to promote the attachment of rat kidney fibroblasts to fibronectin. Free RGDS peptide (SEQ ID NO: 24) inhibits attachment of cells to fibronectin-coated substrates. The RGDS sequence (SEQ ID NO: 24) is also a target for infectious agents (Treponema's syphilis, Mycobacterium's tuberculosis). RGDS (SEQ ID NO: 24 can also block fibrinogen-induced aggregation of intact erythrocytes and specific binding of fibrinogen to erythrocyte membranes.

The production of the PEG-linker-(BX)n conjugate can be done, for example, simply by mixing the respective peptide with the maleimide-functionalized, carboxylic acid-functionalized, or amino-functionalized PEG under conditions which permit the conjugate formation. For example, the thiol group of a cysteine residue of the linker peptide can be used to link the peptides to maleimide-functionalized PEG by Michael-type addition reaction. Alternatively, to modify the amino-functionalized PEG with azide, the resulting polymer will allow the conjugation of alkyne-containing peptide through click chemistry.

When the conductive hydrogel according to the invention comprises PEDOT:PSS as the conductive polymer, the PEG-(BX)n conjugate is preferably selected from 5 kD-PEG-KA7, 10kD-PEG-KA7, or 20 kD-PEG-KA7. Interestingly, the gelation rates of conjugates with linear PEG were slower than using the starPEG/PEDOT:PSS conjugate system, and efficient mixing led to forming homogeneous hydrogels, which is preferred according to the invention.

It should be noted that in the PEG-peptides, which are disclosed herein without a specific linker or linker sequence, the linker is L1 (CWGG) by default, e.g. 5 kD-PEG-KA7 is 5 kD-PEG-CWGG-KA7.

When the conductive hydrogel according to the invention comprises rGO:PSS or rGO:PEDOT:PSS as the conductive polymer, the PEG-(BX)n-conjugate is preferably starPEG-KA7, wherein starPEG is most preferably a 4-arm starPEG.

Most preferably, the conductive hydrogel according to invention comprises a PEG-linker-(BX)n conjugate selected from 5 kD-PEG-L2-KA7, 10 kD-PEG-L2-KA7 and 20 kD-PEG-L2-KA7 and the conductive polymer PEDOT:PSS.

In a further embodiment of the invention, conductive hydrogels are preferred, which comprise 0.01 mM to 10 mM PEG-L1-(BX)n or 0.01 mM to 10 mM PEG-L2-(BX)n, preferably 0.5 mM to 2.5 mM PEG-L1-(BX)n or 0.5 mM to 2.5 mM PEG-L2-(BX)n.

In another preferred embodiment, the content of PEDOT:PSS in the conductive hydrogel of the invention is in the range of 0.01% to 10%, more preferably in the range of 0.1% to 2%. The content of rGO:PSS or rGO:PEDOT:PSS is suitably in the range of 0.01% to 10%, more preferably in the range of 0.1% to 2%.

Mechanical robustness of the conducive hydrogel of the invention depends inter alia on the type of the polystyrene sulfonate compound, peptide sequence, and the type and chain length of PEG comprised in the hydrogel. Mechanical robustness is for example represented by the stiffness of the hydrogels and can be measured with the storage modulus. The rGO:PEDOT:PSS/starPEG-KA7 hydrogel is mechanically more robust than the rGO:PSS/starPEG-KA7 hydrogel. The rGO:PEDOT:PSS/starPEG-KA7 hydrogel has shown a storage modulus of 2000 Pa, while the storage modulus of the rGO:PSS/starPEG-KA7 hydrogel is below 100 Pa. When KA7 peptide is conjugated to 5 k linear PEG, mixing 5 kD-PEG-KA7 and rGO:PEDOT:PSS led to very soft hydrogel (<100 Pa). Reducing the PEG chain length causes increase of storage modulus. 5 kD-PEG-KA7/PEDOT:PSS hydrogel is remarkably stiffer than 10 kD-PEG-KA7/PEDOT:PSS and 20 kD-PEG-KA7/PEDOT:PSS hydrogels.

Mechanical robustness of the conducive hydrogel of the invention depends further on the concentrations of the ingredients used. For example, the 5 kD-PEG-KA7/PEDOT:PSS hydrogel formed at higher concentrations is mechanically more stable and elastic and shows an increased storage modulus. For example, repeatedly pressing the hydrogel formed by mixing 2.5 mM 5 kD-PEG-KA7 and 1% PEDOT:PSS caused deformation and recovery of original shape after the stress was removed. When 0.5 mM 5 kD-PEG-KA7 was used, the resulting material was more fragile.

Mechanical robustness of the conducive hydrogel of the invention depends further on the oligopeptide comprised in the hydrogel. For example, the use of the KG7 oligopeptide reduced the storage modulus drastically, compared to the use of the KA7 oligopeptide.

Accordingly, the stiffness and thus the storage modulus of the conductive hydrogel according to the invention can be tuned by using different polystyrene sulfonate compounds and/or PEGs of different chain length/molecular weight and further by varying the concentrations of the PEG-(BX)n conjugate and the polystyrene sulfonate compound and/or the type of the (BX)n oligopeptide used. Therefore, it as a great advantage of the conductive hydrogel of the invention that its stiffness can be adapted to its desired function, i.e. for drug release purposes or providing an ECM for encapsulation and growing/differentiating cells.

Likewise, the conductivity of the hydrogels of the invention can be tuned and adapted to desired functions. For example, by increasing the number of (KA), repeats the impendency decreased gradually. For example, hydrogels comprising oligopeptides with a lower number of (BX)n repeats were less conductive. Strongly crosslinked network can enhance the conductivity. However, changing the PEG chain length has little influence on the conductivity. The conductivity of the hydrogel is further influenced by the concentration of the polystyrene sulfonate compound in the hydrogel.

Corresponding to a specifically preferred embodiment of the present invention, the hydrogel matrix comprises in addition a highly negatively charged oligosaccharide. According to this embodiment, an oligosaccharide/oligopeptide/conductive polymer/PEG-system exists where the oligopeptide is chemically conjugated to the PEG and the gel formation is carried out through mixing the oligopeptide-polymer-conjugate, the conductive polymer and the oligosaccharide. The non-covalent macromolecular self-organization is also induced by the interaction of the oligopeptide, the conductive polymer and the oligosaccharide. The choice of the PEG and the oligosaccharide can lead to various gel properties including the flow behavior, the gelling condition and the gelling speed as well as adjustable affinity of peptides interacting with bioactive proteins, for example, growth factors and the like. However, variability in gel properties is also realized through changes of a the peptide sequence motif linker-(BX)n, wherein according to the concept of the present invention the corresponding hydrogel matrix is principally also possible without oligosaccharide. In this manner, the flexible design of the oligopeptide sequence can lead to a broad variety of gel properties, that not only lead to the above-stated rheological properties, the gelling condition, the gelling speed and protein binding properties, but also leads to properties such as for example, the biological degradation due to proteolytic hydrolysis or other enzymatic activity such as light impact sensitivity.

The highly negatively charged oligosaccharide, according to an advantageous embodiment, is a sulfated or phosphorylated oligosaccharide, preferably selected from a group of oligosaccharides which comprises heparin, dextran sulfate, α-cyclodextrin sulfate, β-cyclodextrin sulfate, γ-cyclodextrin sulfate, α-cyclodextrin phosphate, β-cyclodextrin phosphate, γ-cyclodextrin phosphate, heparan sulfate, chondroitin sulfate, dermatan sulfate and keratin sulfate. In an especially preferred embodiment for an oligosaccharide/peptide/polymer system the hydrogel matrix comprises heparin as oligosaccharide, which originates from the mucosa of pig intestine or bovine lung tissue. Heparin is preferably of pharmaceutical quality. In an alternative embodiment the hydrogel matrix comprises dextran sulfate as oligosaccharide, which preferably has a molecular weight in the range of 4 kD to 600 kD. Preferred is the use of dextran sulfate of pharmaceutical quality. If the hydrogel matrix contains cyclodextrin sulfate, then it is preferably α-cyclodextrin sulfate, β-cyclodextrin sulfate, γ-cyclodextrin sulfate of pharmaceutical quality, wherein the sulphation degree of three sulfates per molecule up to a complete sulphation degree. If the hydrogel matrix contains α-cyclodextrin phosphate, β-cyclodextrin phosphate, γ-cyclodextrin phosphate then it is of pharmaceutical quality, wherein the degree of phosphorylation of three phosphate groups per molecule can be up to the complete phosphorylation.

The conductive hydrogel according to invention, with the composition as described herein has several advantageous characteristics. In one aspect, the conductive hydrogel is highly resistant against deionized water, DMF, DMSO, ethanol, 1M HCl and 1 M NaOH. In a further aspect, the conductive hydrogel of the invention has self-healing and shear-thinning properties, which is a prerequisite for their injectability. In a third aspect, the conductive hydrogel of the invention, the rheological properties and electrical impedance are tunable.

The conductive hydrogel of the invention shows a very good biocompatibility and has the advantage of a defined chemical composition. The conductive hydrogel of the invention is thus broadly applicable in biomedicine.

In a further embodiment of the invention, the conductive hydrogel is capable of forming a conductive 3D matrix, which is especially suitable for providing conductive hydrogel beads for the targeted release of therapeutic reagents, wherein via a corresponding method therapeutic reagents may be entrapped or encapsulated within the above-described conductive hydrogel matrix or the above-described conductive hydrogel beads. The group of each of the utilized therapeutic reagents comprises preferably cells or organoids (e.g. mesensphere, neurosphere) or a morphogen or an active pharmaceutical ingredient.

When the conductive hydrogel according to the invention comprises cells as the therapeutic agent, the cells are typically mammalian cells, insect cells, bacteria or yeast cells, preferably mammalian cells, most preferably human cells or human cell lines. In a particularly preferred embodiment, the cells are fibroblast cells, mesenchymal stromal cells (MSC), neuronal progenitor cells (NPC) or human umbilical vein endothelial cells (HUVEC).

An organoid is a miniaturized and simplified version of an organ produced in vitro in three dimensions that shows realistic micro-anatomy. Organoids are derived from one or a few cells from a tissue, embryonic stem cells or induced pluripotent stem cells, which can self-organize in three-dimensional culture owing to their self-renewal and differentiation capacities.

The 3D conductive hydrogel matrix of the present invention can provide a convenient in vitro model for the study of complex cell-cell and cell-matrix interactions in the absence of exogenous substrates and may benefit the development of regenerative medicine strategies, which is not possible with traditional cell culture methods which rely on growing cells as monolayers. Mesenchymal stem cell (MSC) spheroids, or "mesenspheres" of different sizes can be formed and maintained in the 3D conductive hydrogel matrix of the present invention. 3D culturing of mesenspheres have been shown to exhibit no evidence of cell necrosis or differentiation, while mesenspheres in differentiation media exhibited differentiation similar to conventional 2D culture methods based on histological markers of osteogenic and adipogenic commitment. Furthermore, when plated onto tissue culture plates, cells that had been cultured within mesenspheres in growth medium recovered morphology typical of cells cultured continuously in adherent monolayers and retained their capacity for multi-lineage differentiation potential. In fact, more robust matrix mineralization and lipid vacuole content were evident in recovered MSCs when compared to monolayers, suggesting enhanced differentiation by cells cultured as 3D spheroids. Thus, a 3D culture system for mesenchymal stem cells may circumvent limitations associated with conventional monolayer cultures and enhance the differentiation potential of multipotent cells (Baraniak P. R., McDevitt T. C., Scaffold-free culture of mesenchymal stem cell spheroids in suspension preserves multilineage potential. Cell Tissue Res. 2012 March; 347(3):701-11).

The 3D conductive hydrogel matrix of the present invention can further provide a convenient environment to produce neurospheres. A neurosphere is a culture system composed of free-floating clusters of neural stem cells. Neurospheres provide a method to investigate neural precursor cells in vitro. Putative neural stem cells are suspended in a medium lacking adherent substrates but containing necessary growth factors, such as epidermal growth factor and fibroblast growth factor. This allows the neural stem cells to form into the characteristic 3-D clusters. A typical use of the neurosphere is in neurosphere assays.

It has been shown that cells disperse evenly in the 3D matrices. Remarkably, cells grew better in PEG-(BX)n/PSS hydrogels of final concentrations of 500 µM and 1% respectively (0.5 mM/1% hydrogel), as compared to 1 mM/2% hydrogel and 2 mM/2% hydrogels. It is important to note that the 0.5 mM/1% hydrogel is relatively more transparent than the 1 mM/2% and 2 mM/2% hydrogels. This makes it possible to image cells in the dark matrix using light and fluorescence microscopes, while strong light absorption is an intrinsic property of such conductive large aromatic systems. Therefore, for the purpose of encapsulating cells into the conductive hydrogel of the invention, the use of PEG-(BX)n/PSS hydrogels with final concentrations of 500 µM and 1% respectively (0.5 mM/1% hydrogel), for example of 5 kD-PEG-KA7/PEDOT:PSS (0.5 mM/1%) is most preferred.

In a further advantageous embodiment, it is possible with the conductive hydrogel of the invention differentiate cells, for example, to differentiate MSCs to cardiomyocytes under electric stimulation (ES) conditions. It has been shown that, upon encapsulation in the conductive 3D matrix, MSCs develop into mesensphere-like structures, whereas ES drives the cells to differentiate into myocardiocyte-like cells.

A morphogen is a substance whose non-uniform distribution governs the pattern of tissue development in the process of morphogenesis or pattern formation, one of the core processes of developmental biology, establishing positions of the various specialized cell types within a tissue. More specifically, a morphogen is a signaling molecule that acts directly on cells to produce specific cellular responses depending on its local concentration.

Typically, morphogens are produced by source cells and diffuse through surrounding tissues in an embryo during early development, such that concentration gradients are set up. These gradients drive the process of differentiation of unspecialized stem cells into different cell types, ultimately forming all the tissues and organs of the body. The control of morphogenesis is a central element in evolutionary developmental biology.

Mammalian morphogens suitable for use in the conductive hydrogel of the invention include retinoic acid, sonic hedgehog (SHH), transforming growth factor beta (TGF-β)/bone morphogenic protein (BMP), and Wnt/beta-catenin. During development, retinoic acid, a metabolite of vitamin A, is used to stimulate the growth of the posterior end of the organism. Retinoic acid binds to retinoic acid receptors that acts as transcription factors to regulate the expression of Hox genes. Exposure of embryos to exogenous retinoids especially in the first trimester results in birth defects. TGF-β family members are involved in dorsoventral patterning and the formation of some organs. Binding to TGF-β to type II TGF beta receptors recruits type I receptors causing the latter to be transphosphorylated. The type I receptors activate Smad proteins that in turn act as transcription factors that regulate gene transcription. Sonic hedgehog (Shh) are morphogens that are essential to early patterning in the developing embryo. Shh binds to the Patched receptor which in the absence of Shh inhibits the Smoothened receptor. Activated smoothened in turn causes Gli1, Gli2, and Gli3 to be translocated into the nucleus where they activate target genes such at PTCH1 and Engrailed.

When the conductive hydrogel according to the invention comprises an active pharmaceutical ingredient as the therapeutic agent, the active pharmaceutical ingredient is typically selected from anti-cancer compounds, anti-coagulation compounds, anti-inflammatory compounds, immune-suppressive compounds, therapeutic antibodies, diagnostic reagents, hormones, growth factors, cytokines, small molecules as inhibitors for growth factors, small molecules as inhibitors for cytokines, aptamer-inhibitors for growth factors and aptamer-inhibitors for cytokines. In a particularly preferred embodiment, the active pharmaceutical ingredient is selected from doxorubicin, paclitaxel, cyclosporin A, tacrolimus, rapamycin, anti-VEGF antibody, and anti-TNF-α antibody.

When the conductive hydrogel according to the invention comprises a morphogen as the therapeutic agent, the morphogen is typically selected from TNF-α, TGF-β, IFN-γ, FGF, VEGF, and EGF.

One can further enhance the biomimetic nature of the conductive hydrogel of the present invention, by the incorporation of growth factor binding domains. For example, heparin-binding peptides can be employed to bind heparin, which can in turn be employed to bind morphogens, for example heparin-binding growth factors, such as TNF-α, TGF-β, IFN-γ, FGF, VEGF, and EGF. As such, if the heparin-binding growth factor, heparin, and the activated heparin-binding peptide were mixed with the PEG (similarly as described in the subsequent section), the resulting gel will slowly release the growth factor, holding most of it until an invading cell released the growth factor by degradation of the gel. This is one of the natural functions of the extracellular matrix in vivo, to serve as a depot for growth factors which become released in injury by local cellular activity. Different anionic polymers used in the invention to form non-covalent hydrogel, including PEDOT:PSS, rGO:PSS and PEDOT:rGO:PSS, have moderate to potent affinity to the heparin binding proteins. Therefore, they can cause effect for affinity capture and controlled release of morphogens, cytokines, as well as drugs in a manner similar to heparin hydrogels. Another related way to sequester heparin-binding growth factors would be more directly through the use of covalently incorporated heparin mimics, for example, peptides with negatively charged side chains that directly bind growth factors. Moreover, since the biomaterial itself is a network, it can be used to release a growth factor that is simply physically incorporated and is released slowly by degradation or diffusion, or a combination thereof. It should be understood that, because the gelation chemistry is self-selective, the growth factor itself and the other bioactive peptides are not chemically modified so as to destroy their biological activity. This important aspect of self-selectivity obviates the need, for example, to encapsulate the growth factor in polymer particles (to thereby protect it from the gelation chemistry, if the gelation chemistry were to react with side groups that are present free on the growth factor, such as the epsilon amines present on the side chains of lysine in the protein).

Hydrogels are particularly useful for the delivery of drugs, in particular protein therapeutics. Hydrogels are biocompatible, and provide a gentle environment for proteins to minimize denaturation of the proteins. The proteins are physically entrapped within the gels. Additionally, degradable can be incorporated within the polymers that form the hydrogel, and via degradation of segments within the gel, the proteins will be released as the gel degrades. A particularly useful embodiment of the invention occurs in the case when the conjugate addition reaction itself leads to a structure that is particularly prone to hydrolysis.

In a further advantageous embodiment, the conductive hydrogels of the invention can be further used to encapsulate and release hydrophobic as well as charged hydrophilic compounds, because the networks of PEG-peptide/PEDOT:PSS hydrogels and the PEG-peptide/rGO:PEDOT:PSS hydrogels are amphipathic. For example, Doxorubicin can be encapsulated with a concentration as high as 0.8 mg/ml, while 1 mg/ml paclitaxel can be encapsulated into the hydrogel.

The invention further relates to processes for preparing a conductive hydrogel according to the invention.

In a first aspect, said process for preparing a conductive hydrogel according to the invention comprises the steps of
i) preparing a conjugate of polyethylene glycol (PEG) and a linker-(BX)n oligopeptide of formula (I):

PEG-linker-(BX)n    (I), wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20;
ii) mixing said conjugate of polyethylene glycol (PEG) and an oligopeptide of formula (I) with a polystyrene sulfonate compound;
iii) forming the conductive hydrogel matrix by gelation.

It should be recognized that the advantages and advantageous embodiments described above for the conductive hydrogel according to the invention equally apply to the processes for preparing said conductive hydrogel such that it shall be referred to the above.

In a more preferred embodiment, said conjugate of formula (I) is PEG-L1-(BX)n or PEG-L2-(BX)n.

(BX)n is most preferably the KA7 peptide of SEQ ID NO: 3.

PEG is most preferably selected from starPEG-5 k, starPEG-10 k, linear PEG-5 k, linear PEG-10 k and linear PEG-20 k.

Said polystyrene sulfonate compound is more preferably selected from PEDOT:PSS, rGO:PSS and rGO:PEDOT:PSS. Most preferably, said polystyrene sulfonate compound is PEDO:PSS.

Step ii) of mixing the conjugate of polyethylene glycol (PEG) and an oligopeptide of formula (I) and the polystyrene sulfonate compound is a very simple process and is preferably performed in aqueous solution.

In a more preferred embodiment, the PEG-L1-(BX)n or PEG-L2-(BX)n compound is contained in the aqueous mixing solution at a final concentration in the range of 0.01 mM to 10 mM, most preferably in the range of 0.5 to 2.5 mM.

In a further, more preferred embodiment, said polystyrene sulfonate compound is contained in the aqueous mixing solution at a final concentration in the range of 0.01% to 10%, most preferably 0.1% to 2%.

The formation of the conductive hydrogel, i.e. the gelation can be performed at a temperature in the range of 0° C. to 50° C. Preferably, the gelation is performed at a temperature in the range of 10° C. to 45° C., 20° C. to 40° C. or 30° C. to 35° C. Most preferably, the gelation is performed at a temperature in the range from room temperature to 37° C.

In a further aspect, the invention provides a process for preparing a conductive hydrogel, which comprises cells or organoids. In this case, the process further comprises the additional steps of:
iv) seeding said cells or organoids on the hydrogel matrix obtained by step iii) as described above; and
v) incubating said hydrogel matrix and said seeded cells or organoids to facilitate cell adhesion to the conductive hydrogel matrix.

Alternatively, the cells or organoids are not added to the already formed conductive hydrogel matrix, but are already added during the process of preparing the conductive hydrogel according to the invention. Thus, in a further aspect, the invention provides process for preparing a conductive hydrogel comprising cells or organoids, said process comprising the steps of:
i) preparing a conjugate of polyethylene glycol (PEG) and a linker-(BX)n oligopeptide of formula (I):

PEG-linker-(BX)n    (I), wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20;
ii) premixing cells or organoids with a polystyrene sulfonate compound in a culture medium;
iii) mixing said conjugate of polyethylene glycol (PEG) and an oligopeptide of formula (I) with the culture medium comprising the cells or organoids premixed with a polystyrene sulfonate compound; and
iv) forming the conductive hydrogel matrix by gelation to encapsulate the cells or organoids into the hydrogel matrix.

In a further preferred embodiment, the conductive hydrogel matrix containing cells or organoids and prepared by the aforesaid process has a 3D-architecture or 3D structure. Most preferably, the conductive hydrogel matrix containing cells or organoids and prepared by the aforesaid process is sphere-shaped or is present in the form of beads. Spheric shape or bead shape can for example be manufactured by using a microfluidic device. Therefore, in a further aspect, the invention provides a process for preparing a conductive hydrogel comprising cells or organoids, wherein said process optionally comprises the further step of:
v) culturing said cell- or organoid-containing hydrogel matrix.

The culturing of said cell- or organoid-containing hydrogel matrix is typically performed in liquid culture in a culture medium, which supports the growth and development or which maintains the viability of the adhered or encapsulated cells or organoids. Culturing is typically performed at a temperature in the range of in the range of 0° C. to 50° C., preferably in the range of 10° C. to 45° C., 20° C. to 40° C. or 30° C. to 35° C. Most preferably, culturing is performed at a temperature in the range from room temperature to 37° C., which is best for maintaining the viability and/or for growth and further development of the adhered or encapsulated cells.

When cells are provided onto the matrix, $1\text{-}10^6$ cells/cm$^2$, preferably 10 to $10^6$ cells/cm$^2$ more preferably $10^2$ to $10^5$ cells/cm$^2$, most preferably $10^3$ to $10^5$ cells/cm$^2$ are seeded onto the conductive hydrogel of the invention.

When cells are encapsulated into the matrix, $1\text{-}10^{10}$ cells/mL, preferably 10 to $10^9$ cells/mL, more preferably $10^2$ to $10^8$ cells/mL, most preferably $10^3$ to $10^7$ cells/mL are used for cell encapsulation.

A typical culture medium, in which the cells are grown and provided for seeding onto or into the conductive hydrogel of the invention is DMEM (Dulbecco's Modified Eagle Medium, Gibco), preferably DMEM containing 10% FBS Fetal Bovine Serum).

In a further aspect of the invention, a process for preparing a conductive hydrogel is provided, wherein said conductive hydrogel comprises a morphogen or an active pharmaceutical ingredient. Such a process comprising the steps of:

i) preparing a conjugate of polyethylene glycol (PEG) and a linker-(BX)n oligopeptide of formula (I):

PEG-linker-(BX)n  (I), wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20;

ii) premixing an active pharmaceutical ingredient or morphogen with a polystyrene sulfonate compound in solution, preferably in aqueous solution;

iii) mixing said conjugate of polyethylene glycol (PEG) and an oligopeptide of formula (I) of step i) with the solution of step ii) comprising the premixed active pharmaceutical ingredient or morphogen and a polystyrene sulfonate compound;

iv) forming the conductive hydrogel matrix by gelation.

Said active pharmaceutical ingredient is typically contained in the mixture of step iii) in a final concentration of 0.01 µg/l to 2.0 g/l; preferably in the range of 0.1 µg/l to 1.5 g/l, 1.0 µg/l to 1.0 g/l or 10 µg/l to 0.5 g/l, more preferably in the range of 0.1 mg/l to 0.1 mg/l, most preferably in the range of 1.0 mg/l to 0.01 g/l.

In yet a further aspect, the invention provides the use of a conductive hydrogel according to the invention in biomedical applications, such as neuroprostheses, biosensors, nerve grafts, cell culture, cell storage, and drug delivery.

The invention is described in more detail by xy figures and xy working examples.

Example 1: Peptide Synthesis

All peptides mentioned herein are produced by utilizing a standardized-fluorenylmethoxycarbonyl chemistry (FMOC chemistry) on a solid phase with 2-(1H-benzotriazol-1-yl)-1,1,3,3 tetramethyluronoiumhexafluorophosphate-activation (HBTU-activation) in an automatic solid phase peptide synthesizer (ResPep SL, Intavis, Cologne, Germany). To obtain good peptide quality, each amino acid was coupled two times with the fivefold excess, wherein all non-reacting amino groups were protected with acetic acid anhydride. For cleaving the peptide from the resin, the resin was treated for one and one half hour with a mixture of trifluoroacetic acid (TFA) triisopropylsilane(TIS)/water/dithiothreitol (DTT), wherein these components are present in a ratio of 90 (v/v):2.5 (v/v):2.5 (v/v):2.5 (m/v).

The peptides were dissolved in water, which contained 2 mg/ml tris(2-carboxyethyl)phosphine (TCEP). The peptide purification was carried out by means of reverse-phase high pressure liquid chromatography (UPLC) on a preparative HPLC-device (Prostar™, Agilent Technologies, Santa Clara, USA) which was provided with a preparative C18-column (AXIA™ 1001 A grain size 10 µm, 250×30 mM, Phenomenex Torrance USA). The peptide was eluted from the column by utilizing a gradient of 5% to 100% solvent B at 20 ml/min, wherein solvent A is 0.1% trifluoroacetic acid (TFA) in water and solvent B is 0.1% TFA and 5% water in acetonitril.

The purity was confirmed through analytical reverse-phase ultrahigh pressure liquid chromatography (UPLC Aquity™ with UV detector, Waters, Milford Mass., USA) provided with an analytical C18-column (AQUITY™ UPLC BEH C18, grain size 1.7 µm, 50×2.1 mM, Waters, Milford, Mass., USA) by utilizing an isocratic gradient and an electrospray-ionisation-mass-spectrometry (ESI-MS) (AQUITY™ TQ detector, Waters, Milford, Mass., USA). The peptide was dry frozen into a white powder (CHRIST ALPHA™ 2-4 LD plus+ vacuubrand RZ6) and at 4° C. under dry conditions stored for not more than one week prior to further treatment.

Example 2: Synthesis of Peptide-PEG-Conjugates

The synthesis of the PEG-peptide-conjugates for use in the hydrogel self-organization were carried out through Michael-addition-reactions between maleimide-terminal four-armed PEG or maleimide-terminal linear PEG and cysteine-terminal peptides from the library. In the case of star-PEG, both components were dissolved in physiological phosphate buffer solution (1×PBS) with a pH value of 7.4 in a molar ratio of 1:4.5 (star-PEG:peptide) with a total concentration of 80 mg/ml. The reaction mixture was quickly covered and stirred at 750 rpm at room temperature for 18 hours (MR Hei-Standard, Heidolph, Schwabach, Deutschland) The raw products were analyzed through reverse-phase high pressure liquid chromatography (UPLC) (UPLC Aquity™ with UV detector, Waters, Milford, Mass., USA) by using C18 column (AQUITY™ UPLC BEH C18, grain size 1.7 µm, 50×2.1 mM, Waters, Milford, Mass., USA) and an isocratic gradient. The raw product was dialyzed with a dialysis membrane with cut-off limit (cut-off) of 8 kD for two days against 10 liters of water under constant water exchange to release unbound peptides and salt. Thereafter, the product was again injected into the UPLC in order to examine the purity as compared to the analysis before the dialysis. The dialyzed product was dry frozen in water into a solid.

Example 3: Production of the Hydrogel Networks Containing Star-PEG and Heparain 14-kD-heparin (25 mM, 2.5 mM) and star-PEG-peptide conjugates (6.25 mM, 3.125 mM) were dissolved in physiologic phosphate buffer solution (1×PBS) water or cell culture medium with 2% fetal bovine serum (FBS). These solutions were dissolved in a ratio of 1:4 heparin:star-PEG-peptide-conjugate by obtaining 0.5 mM or 5 mM 14-kDheparin and 2.5 mM or 5 mM star-PEG-peptide. The ligand/mol ratio was 2:1, 1:1 and 1:5 relative to the mol ratio of 14-kD-heparin and the star-PEG-peptide-conjugate. The mixtures were incubated within a time frame of one hour to overnight at room temperature of 37° C. The gelling time spanned from present up to several hours depending on the applied peptide motif. A hydrogel was formed when it survived the addition of physiological phosphate buffer solution (1×PBS) pH 7.4 to the mixture after the incubation of the mixture over the prior night without mixing with the added solution.

Example 4: Preparation of Conductive Hydrogels Comprising PEDOT:PSS

L1-(BX)$_n$ peptides comprising a (BX)n peptide selected from KA7, KA5, KA3, KS7, KG7, RA7, and RG7, where X is alanine, glycine or serine (FIG. 1B), were synthesized. The thiol group of cysteine was used to link the peptides to maleimide-functionalized PEG by Michael-type addition reaction, while the tryptophan was used to facilitate the monitoring during HPLC purification and quantification (supporting information). It was first tested whether sulfated oligosaccharide could be replaced by PEDOT:PSS to form a stable hydrogel. starPEG-KA7 in PBS was mixed with PEDOT:PSS aqueous solution to final concentrations of 2.5 mM and 1%, respectively. Different from the starPEG-KA7/heparin or starPEG-KA7/dextran sulfate system, which gelated gradually and formed homogeneous hydrogels, starPEG-KA7/PEDOT:PSS gelated instantly. The gel formation was too fast for efficient mixing, thus resulted in inhomogeneous hydrogel. The same was observed for starPEG-KA5/PEDOT:PSS and starPEG-RA7/PEDOT:PSS. Whereas starPEG-KG7/heparin did not form a hydrogel, starPEG-KG7/PEDOT:PSS also gelated instantly and formed inhomogeneous hydrogels. These results indicated that PEDOT:PSS provides stronger interaction than heparin and dextran sulfate to assemble PEG and (BX)$_n$-oligomers to form non-covalent networks. As KA7 conjugated to linear PEG-10 k formed very weak hydrogels with heparin, hydrogel formation was tested by mixing PEG-5 k-KA7, PEG-10 k-KA7, or PEG-20 k-KA7 with PEDOT:PSS. Interestingly, the gelation rates were slower than using the starPEG-KA7/PEDOT:PSS system, and efficient mixing led to forming homogeneous hydrogels. Without conjugation to the oligopeptide, neither maleimide-functionalized nor amino-functionalized PEG formed a hydrogel with PEDOT:PSS.

Figure 1A:
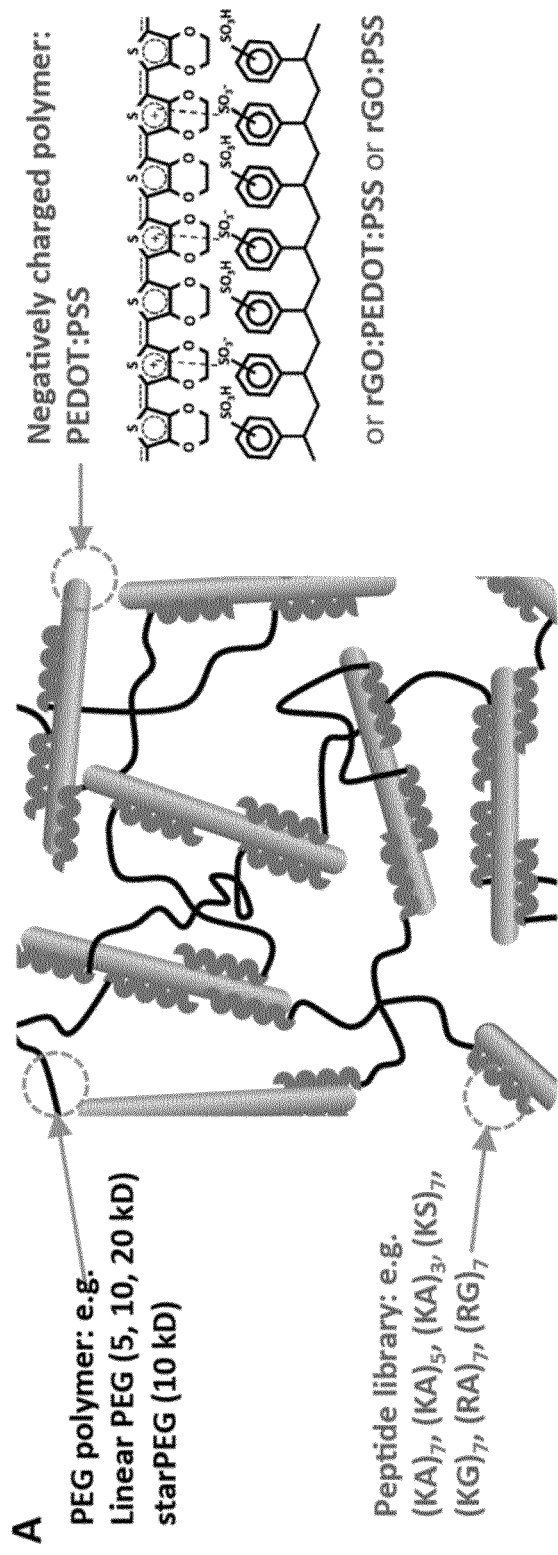
FIG. 1 shows the principal composition of the conductive hydrogel of the invention comprising a PEG, negatively charged polymers and an oligopeptide (1A).
FIG. 1B shows the results of the investigation of the gel formation using different PEGs and different oligopeptides with PEDOT:PSS.

Whereas branched PEG can increase the crosslinking degree, linear PEGs are cheaper and possess narrower molecular weight distribution. Moreover, it is much easier to separate a linear PEG chain with two peptides from that with only one peptide, as compared to purify the starPEG with 4 peptides from a mixture of lower degree of modification. Therefore, in the following study, the hydrogel formation using linear PEG-peptides was investigated. As shown in FIG. 1B, when coupled to PEG-5 k, the (BX)n oligopeptides KA7, KA5, KA3, KS7, KG7, RA7, RG7 all formed homogeneous hydrogels with PEDOT:PSS. To incorporate a cell adhesive motiv into the modular network, the RGDSP (SEQ ID NO: 25) sequence was added as part of the linker to the KA7 oligopeptide. The resulting 5 kD-PEG-L2-KA7, 10 kD-PEG-L2-KA7 and 20kD-PEG-L2-KA7 all formed homogeneous hydrogels with PEDOT:PSS. L2 contains the RGDSP (SEQ ID NO: 25) sequence.

Example 5: Stability, Self-Healing and Mechanical Properties of the Conductive Hydrogels Like the hydrogels using sulfated oligosaccharides, the PEDOT:PSS containing hydrogels are very stable. No degradation could be observed after incubating the biomaterials in PBS buffer or cell culture medium over a period up to half a year. The hydrogels were also resistant to harsh conditions such as deionized water, DMF, DMSO, ethanol, 1 M HCl, and 1 M NaOH. Whereas adding TFE (trifluoroethanol) to starPEG-KA7/heparin hydrogel dissolved the matrix through destroying the α-helical structure of KA7, treating 5 kD-PEG-KA7/PEDOS:PSS hydrogel with TFE caused the hydrogel to break into fragile pieces. In good agreement with the rheological studies shown below, the secondary structure of KA7 is beneficial but not essential for forming stable networks with PEDOT:PSS. When 5 kD-PEG-KA7 is <2.5 mM and PEDOT:PSS is 1%, the resulting hydrogel is smaller than the initial volume, leaving a layer of supernatant above the hydrogel. The syneresis effect reflects the minimum cross-linking density required for the non-covalent network. The non-covalently cross-linked network was also stable after drying. After adding PBS to the vacuum-dried materials, they recovered their original volumes gradually over a time period of about 5 hours.

Figure 2C:
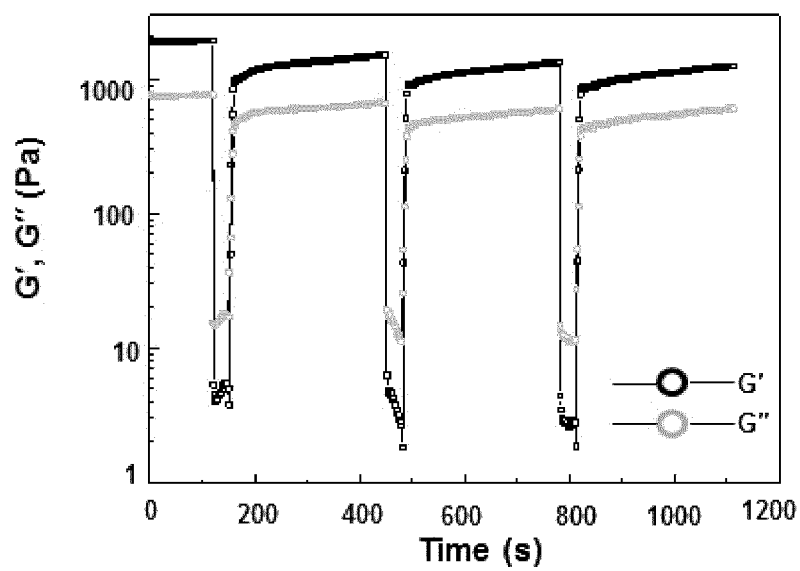
FIG. 2C shows the instant recovery of the hydrogel characteristics (G'>>G") after a strong strain to break the hydrogel was applied.
Figure 2D:
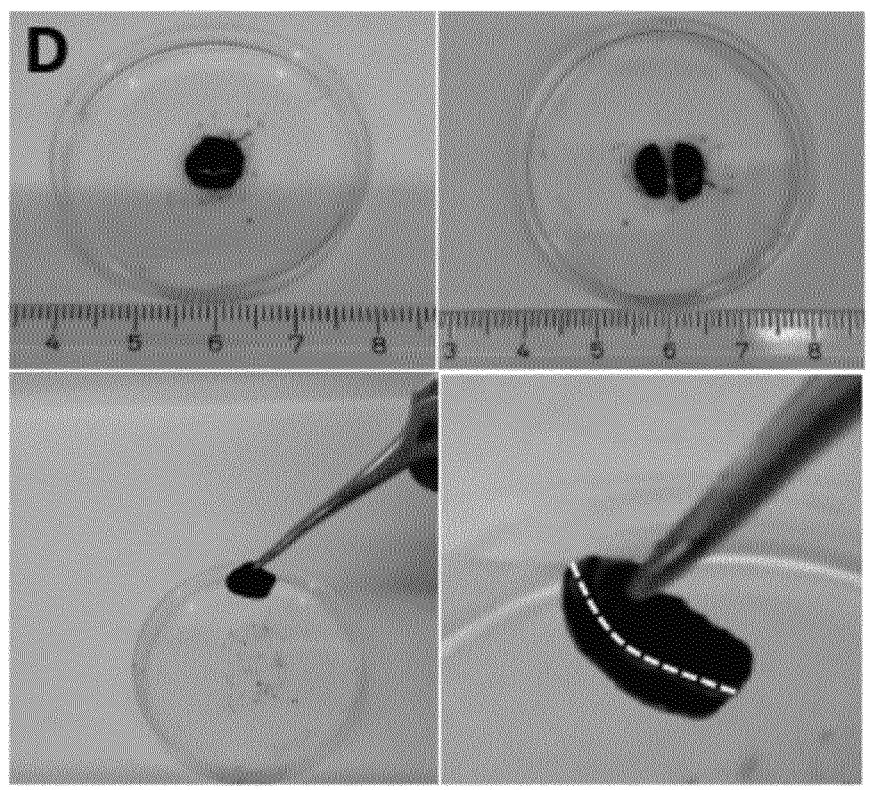
FIG. 2D shows the self-healing of a conductive hydrogel that was cut into half sections in aqueous solution and then placed together.
Figure 2:
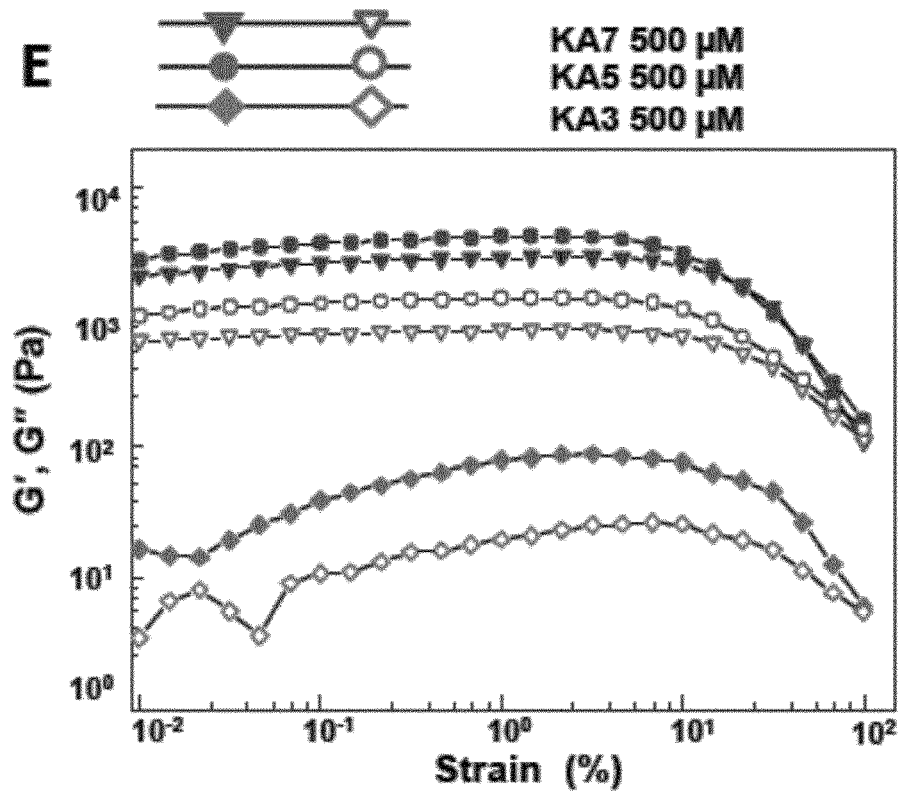
FIG. 2A shows the recovery of the original shape of a 5 kD-PEG-KA7/PEDOT:PSS (2.5 mM/1%) hydrogel after repeatedly pressing the hydrogel.
FIG. 2B shows that the pre-formed conductive hydrogel could be loaded to a syringe and extruded from the needle and thus demonstrates the injectability of the hydrogel.
FIG. 2E shows that by increasing the number of $(KA)_n$ repeats the hydrogel stiffness increases gradually. The concentration of PEDOT:PSS is 1%. 5 kD linear PEG was used.
FIG. 2F shows that reducing the linear PEG chain length causes increase of storage modulus. The concentration of PEDOT:PSS is 1%.
FIG. 2G shows that changing the concentrations of 5 kD-PEG-KA7 and PEDOT:PSS can affect the hydrogel stiffness. High concentrations of 5 kD-PEG-KA7 and PEDOT:PSS lead to stiff hydrogels.
FIG. 2H shows that the hydrogel rheology is dependent on the peptide sequences. The concentration of PEDOT:PSS is 1%. 5 kD linear PEG was used.
FIG. 2I shows that 5 kD-PEG-CWGGRGDSP-KA7 formed stable hydrogel with PEDOT:PSS, showing 10-time reduced storage modulus, as compared to 5 kD-PEG-KA7/PEDOT:PSS. The concentration of PEDOT:PSS is 1%.
FIG. 2J shows that the temperature dependent rheology measurement of 5 kD-PEG-KA7 (500 μM) and PEDOT:PSS hydrogel (1%).

The 5 kD-PEG-KA7/PEDOT:PSS hydrogel formed at higher concentrations is mechanically more stable and elastic. Repeatedly pressing the hydrogel formed by mixing 2.5 mM 5 kD-PEG-KA7 and 1% PEDOT:PSS caused deformation and recovery of original shape after the stress was removed (FIG. 2A). When 0.5 mM 5 kD-PEG-KA7 was used, the resulting material was more fragile. The hydrogel formed by mixing 2.5 mM 5 kD-PEG-KA7 and 1% PEDOT:PSS was also injectable. The pre-formed hydrogel could be loaded to a syringe and extruded from the needle (FIG. 2B). To demonstrate that the injectability is caused by the shear-thinning and self-healing properties of the dynamic network, step-strain rheological measurements using the 5 kD-PEG-KA7/PEDOT:PSS hydrogel was performed. After forming the hydrogel by mixing 2.5 mM 5 kD-PEG-KA7 and 1% PEDOT:PSS, strong strain was applied to break the hydrogel and the recovery of the storage modulus was followed. As shown in FIG. 2C, instant recovery of the hydrogel characteristics (G'>>G") was observed after the applied strain was removed. Full recovery of stiffness occurred after about 20 min. Hydrogel formed by mixing 2.5 mM 5 kD-PEG-KA7 and 1% PEDOT:PSS was cut into half sections in aqueous solution and then placed together (FIG. 2D). After 10 min, the sample self-healed and could be lifted by a tweezers.

Example 6: Rheological Study Using PEDOT:PSS Conductive Hydrogels

A rheological study to investigate the structure-function relationship between chemical composition of the modular system and mechanical properties was performed.

Influence of the (KA)n Repeats

By increasing the number of (KA)$_n$ repeats (FIG. 2E), the hydrogel stiffness increases gradually. 5 kD-PEG-KA7/PEDOT:PSS hydrogel and 5 kD-PEG-KA5/PEDOT:PSS hydrogel exhibit storage moduli of 3,000 Pa and 2,000 Pa respectively, while 5 kD-PEG-KA3/PEDOT:PSS hydrogel is remarkably softer (20 Pa).

Influence of the PEG Chain Length

Figure 2F:
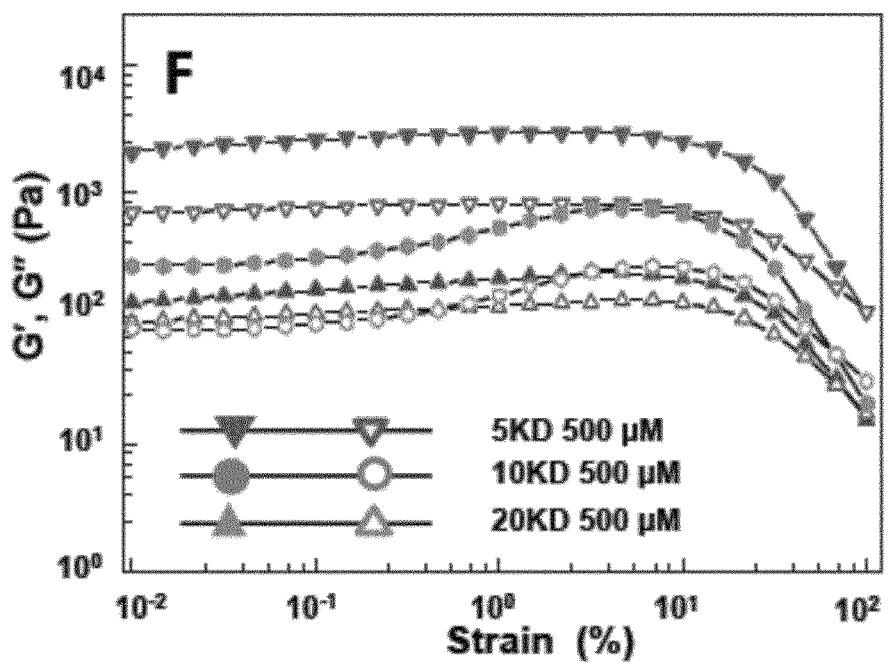

Thereafter, the influence of different polymer chains was tested. Reducing the PEG chain length causes increase of storage modulus. 5 kD-PEG-KA7/PEDOT:PSS hydrogel is remarkably stiffer than 10 kD-PEG-KA7/PEDOT:PSS and 20 kD-PEG-KA7/PEDOT:PSS hydrogels (FIG. 2F). A short polymer chain could cause a more densely packed network. It is important to note that varying the polymer chain and peptide sequence affects not only the final storage modulus, but also the gelation course, indicating the different assembling kinetics ( ).

Influence of the Concentrations of 5 kD-PEG-KA7 and PEDOT:PSS

Figure 2G:
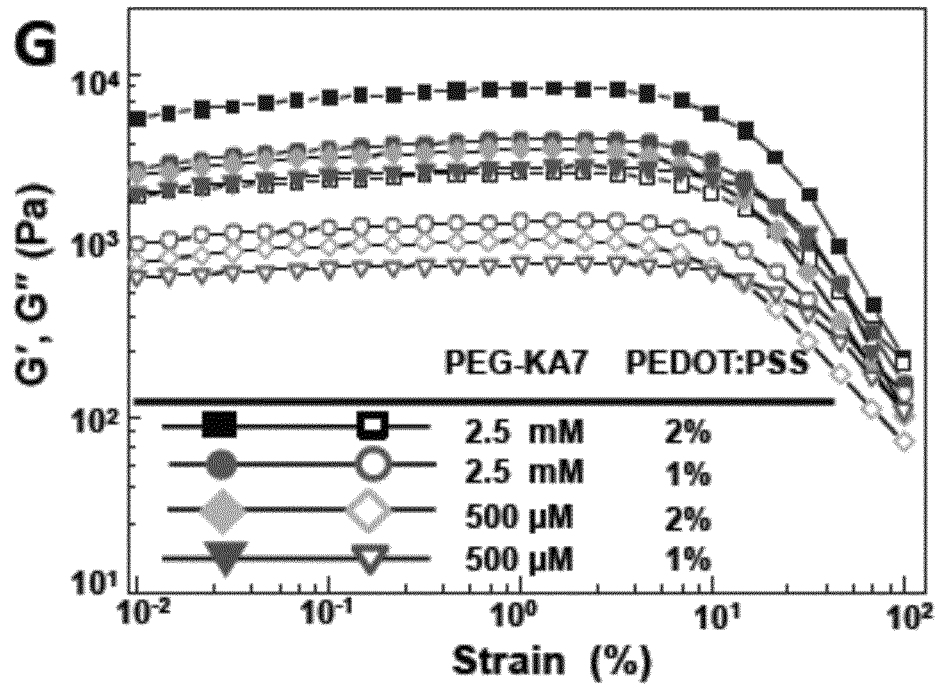

As expected, increasing the concentrations of 5 kD-PEG-KA7 and PEDOT:PSS led to an enhanced storage modulus. The hydrogel formed by mixing 2.5 mM and 2% PEDOT:PSS has shown a storage modulus of 5,000 Pa, while lowering the concentrations resulted in remarkably reduced stiffness (FIG. 2G).

Replacement of (KA)n by (KG)n

Figure 2H:
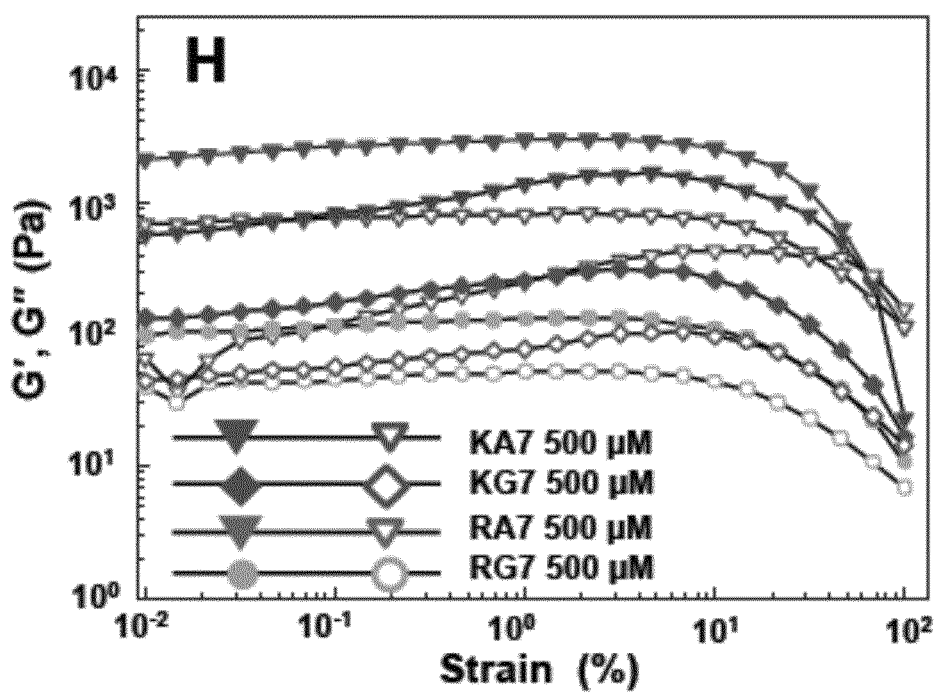

Whereas the (BA), motif is essential for the gelation of peptide-polymer/heparin system, 5 kD-PEG-KG7 forms a hydrogel with PEDOT:PSS. Nevertheless, the use of the KG7 oligopeptide reduced the storage modulus drastically (FIG. 2H and supporting information).

Incorporation of Additional Bioactive Ligands

Figure 2I:
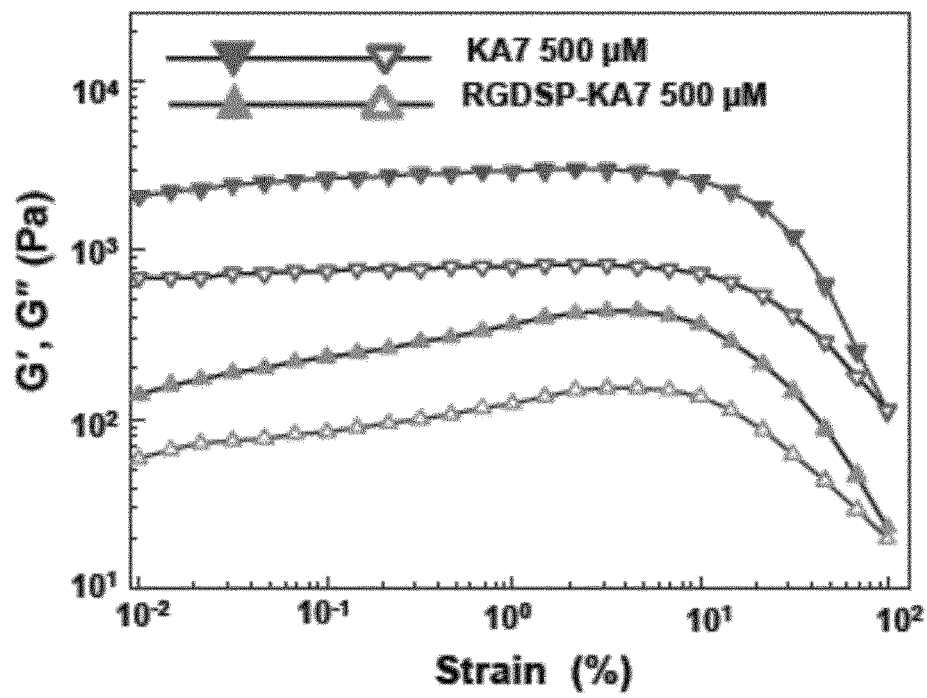

While the modularity of the peptide-polymer system can be used to tune the mechanical properties, it was further investigated whether the incorporation of additional bioactive ligands is possible. The integrin binding peptide RGDSP (SEQ ID NO: 25) has been widely used as a biopolymer modification to enhance cell adhesion. 5 kD-PEG-L2-KA7, in which L2 contains the RGDSP (SEQ ID NO: 25) sequence, was synthesized and it formed stable hydrogel with PEDOT:PSS, showing 10-time reduced storage modulus (FIG. 2I), as compared to 5 kD-PEG-KA7/PEDOT:PSS.

Storage Modulus Versus Temperature Scan

Figure 2J:
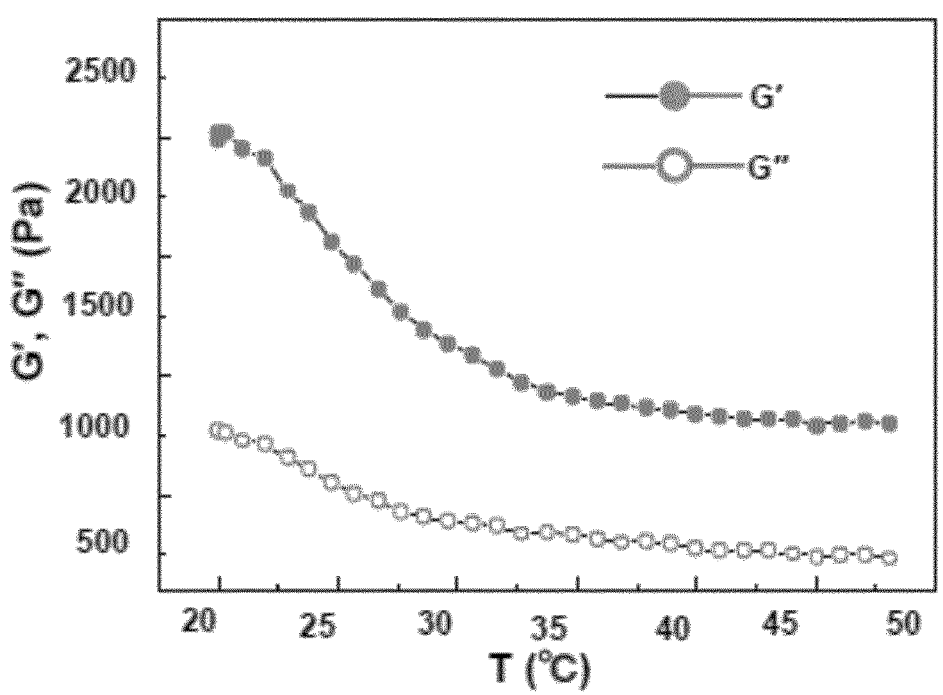

To investigate the hydrogels at elevated temperature for applications such as mammalian cell culture and implantation, we performed a storage modulus versus temperature scan (FIG. 2J). The stiffness of 5 kD-PEG-KA7/PEDOT:PSS hydrogel reduced moderately when the temperature was increased to 50° C., and the hydrogel characteristic (G'>>G") was remained through the temperature scan.

Figure 3A:
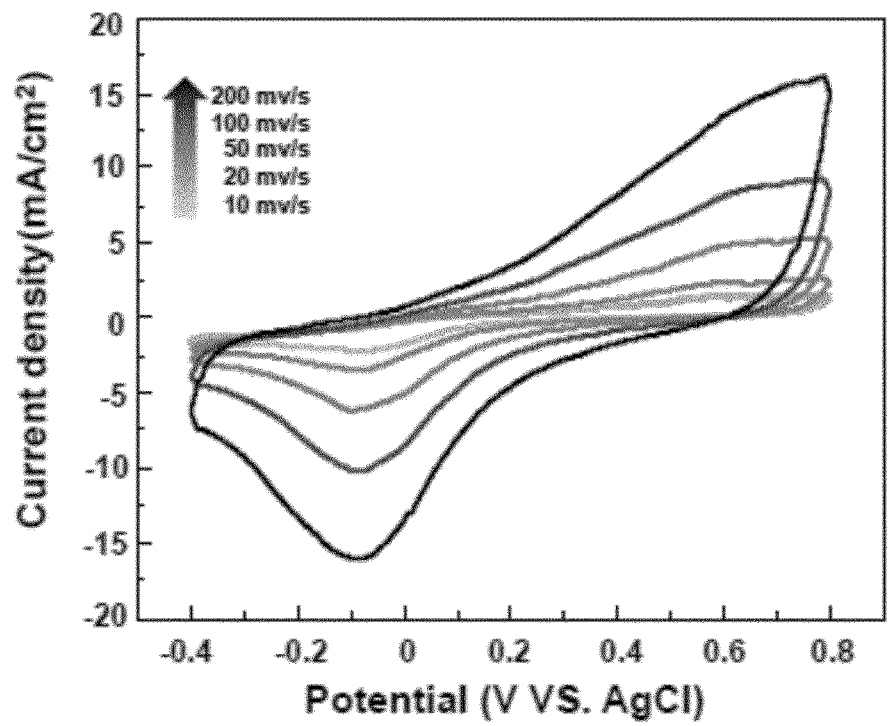
FIG. 3A shows a typical cyclic voltammetry (CV) curve of PEDOT:PSS-based materials (500 μM 5 KD PEG-KA7+ 1% PEDOT:PSS), showing the oxidation peak between +500 mV and +650 mV and reduction occurring between −100 mV and −50 mV. The concentration of 5 kD-PEG-KA7 is 0.5 mM, PEDOT:PSS is 1%.
Figure 3B:
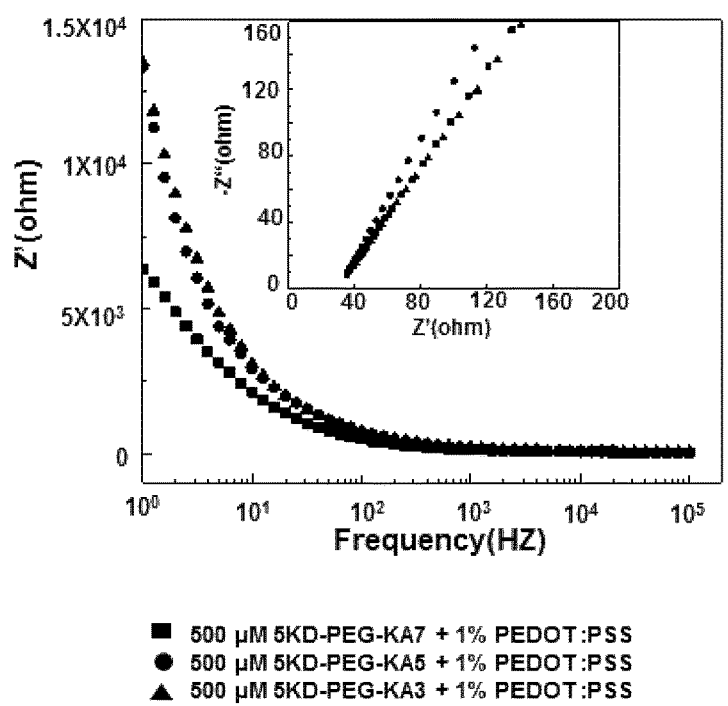
FIG. 3B shows that by increasing the number of $(KA)_n$ repeats, the impendency of the hydrogel decreased gradually.

Example 7: Investigation of the Structure-Function Relationship Between Chemical Composition of the Modular System and Electrochemical Properties The cyclic voltammetry (CV) curve of 5 kD-PEG-KA7/PEDOT:PSS is typical of PEDOT:PSS-based materials, showing the oxidation peak between +500 mV and +650 mV and reduction occurring between −100 mV and −50 mV (FIG. 3A). The structure-function relationship between chemical composition of the modular system and electrochemical properties was investigated Influence of the Number of (KA)n Repeats By increasing the number of (KA), repeats (FIG. 3B), the impendency decreased gradually. 5 kD-PEG-KA7/PEDOT:PSS hydrogel exhibited an impendency of 30 $\Omega cm^2$, while 5 kD-PEG-KA3/PEDOT:PSS and 5 kD-PEG-KA5/PEDOT:PSS hydrogels were less conductive. A strongly crosslinked network can enhance the conductivity.

Influence of the PEG Chain Length

Figure 3C:
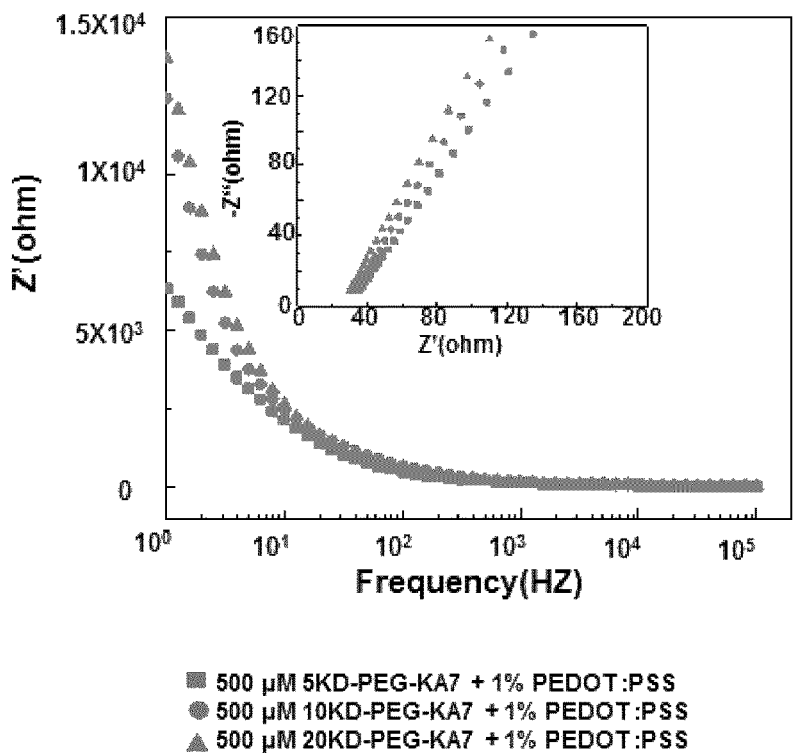
FIG. 3C shows the influence of different polymer chains on the conductivity of the hydrogel. Changing the PEG chain length has little influence on the conductivity. 5 kD-PEG-KA7/PEDOT:PSS, 10 kD-PEG-KA7/PEDOT:PSS and 20 kD-PEG-KA7/PEDOT:PSS hydrogels showed impendency in a similar range.
Figure 3:
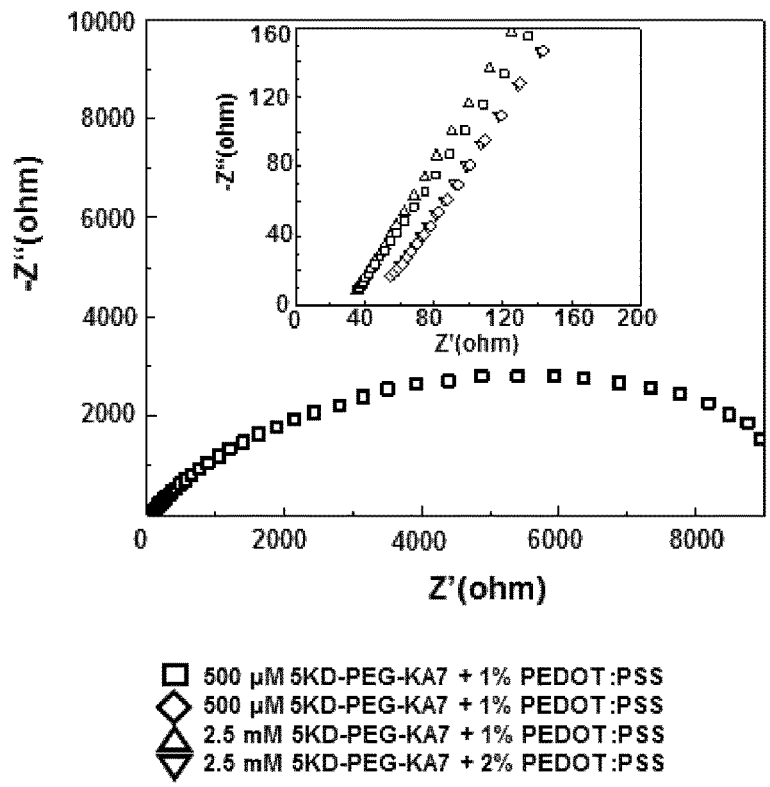
FIG. 3D shows the influence of the concentration of PEDOT:PSS on the conductivity of the hydrogel. Lowering the concentration of PEDOT:PSS resulted in decreased impendency of the non-covalently assembled matrix.
FIG. 3E shows scanning electron microscope (SEM) of 5 kD-PEG-KA7/PEDOT:PSS hydrogel. The conductive materials possess a heterogeneous and porous structure. The concentration of 5 kD-PEG-KA7 is 2.5 mM, PEDOT:PSS is 2%.
FIG. 3F shows transmission electron microscope (left) (TEM) images of 5 kD-PEG-KA7/PEDOT:PSS hydrogel. The conductive materials possess a heterogeneous and porous structure.

Thereafter, the influence of different polymer chains was tested. Changing the PEG chain length has little influence on the conductivity. 5 kD-PEG-KA7/PEDOT:PSS, 10 kD-PEG-KA7/PEDOT:PSS and 20 kD-PEG-KA7/PEDOT:PSS hydrogels (FIG. 3C) showed impendency in a similar range.

Influence of Hydroxyl Groups on the Conductivity of the Hydrogels

It has been reported that the presence of hydroxyl group in PEDOT:PSS based materials can enhance the conductivity. Therefore, 5 kD-PEG-KS7 was synthesized and the 5 kD-PEG-KS7/PEDOT:PSS hydrogel was compared to 5 kD-PEG-KA7/PEDOT:PSS. To replace alanine with serine caused a moderately reduced impendency. Adding the cell adhesive peptide RGDSP (SEQ ID NO: 25) within the linker L2 to 5 kD-PEG-KA7 was found to have a minor effect on the conductivity only.

Influence of the Concentration of PEDOT:PSS

4) Interestingly, lowering the concentration of PEDOT:PSS resulted in decreased impendency of the non-covalently assembled matrix (FIG. 3D). The result was also confirmed in the CV measurements. The mobility of electrons in a network is governed not only by the number of conductive chains, but also the arrangement of the conjugated system and the dopant. Although with less content of conductive polymer, the matrix with 0.5% PEDOT:PSS and 1 mM 5 kD-PEG-KA7 has shown 2-fold decrease of impendency, as compared with the hydrogel formed by mixing 2% PEDOT:PSS and 2.5 mM 5 kD-PEG-KA7.

Example 8: Transmission Electron Microscope (Tem) and Scanning Electron Microscope (SEM)

Figure 3E:
Figure 3E:
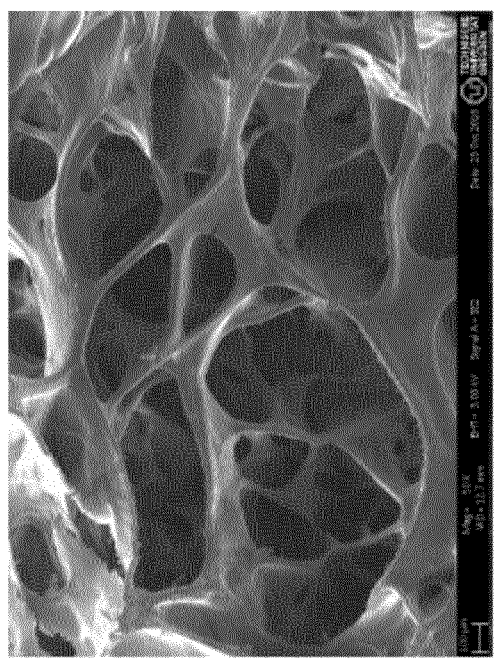
Figure 3F:
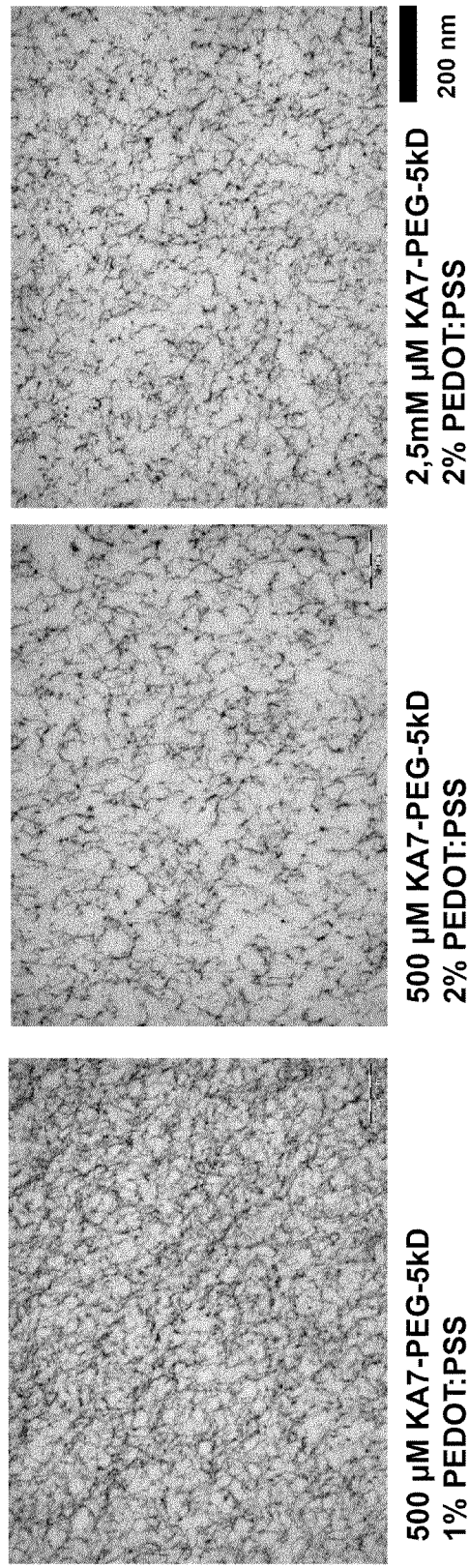

Transmission electron microscope (TEM) and scanning electron microscope (SEM) images of 5 kD-PEG-KA7/PEDOT:PSS hydrogel reveal that the conductive materials possess heterogeneous and porous structure (FIGS. 3E and 3F). Most of the µm-size structures show a dense network at the edge, while the internal matrix is more porous. Interestingly, the hydrogels formed at lower concentrations show nanofibrils with darker contrast, while the regions with higher electron density are thought to mainly consist of crystalline PEDOT phases. In good agreement with the electrochemistry measurements, the hydrogels formed at lower concentrations have denser packing of PEDOT, leading to higher conductivity.

Example 9: Influence of Heparin on Conductive Hydrogels Comprising PEDOT:PSS

The design of PEG-peptide/PEDOT:PSS system aims to provide a bio-matrix system with conductive property through replacing negatively charged oligosaccharide with PEDOT:PSS. The possibility to combine PEDOT:PSS with naturally occurring oligosaccharide was tested in order to realize seamless transition between organic conductive polymer and biomatrix. To form hybrid matrices by pre-mixing heparin with PEDOT:PSS was investigated, while starPEG- KA7 was used. Stable hydrogel was formed. Interestingly, the presence of 1 mM heparin enhanced the conductivity of hydrogel containing 1% PEDOT:PSS and 2.5 mM starPEG-KA7, as compared with the hydrogel formed by mixing 1% PEDOT:PSS and 2.5 mM 5 kD-PEG-KA7.

Example 10: Utility of Conductive Hydrogel Systems for Cell Culture

Culturing Cells on the Conductive Hydrogels

Figure 4A:
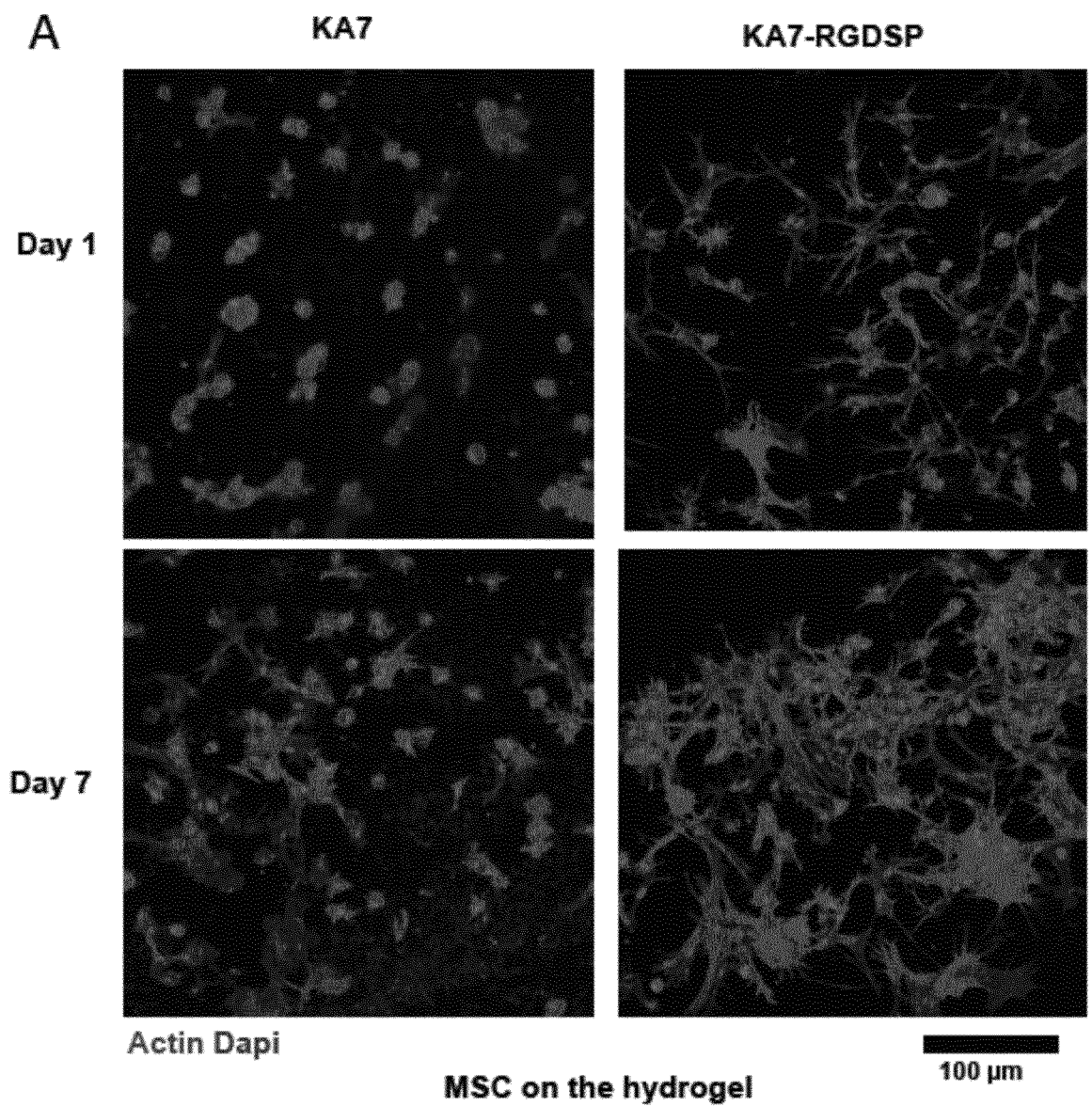
FIG. 4A shows that MSC can attach and proliferate better on 5 kD-PEG-CWGGRGDSP-KA7/PEDOT:PSS hydrogel than on 5 kD-PEG-KA7/PEDOT:PSS hydrogel.
Figure 4B:
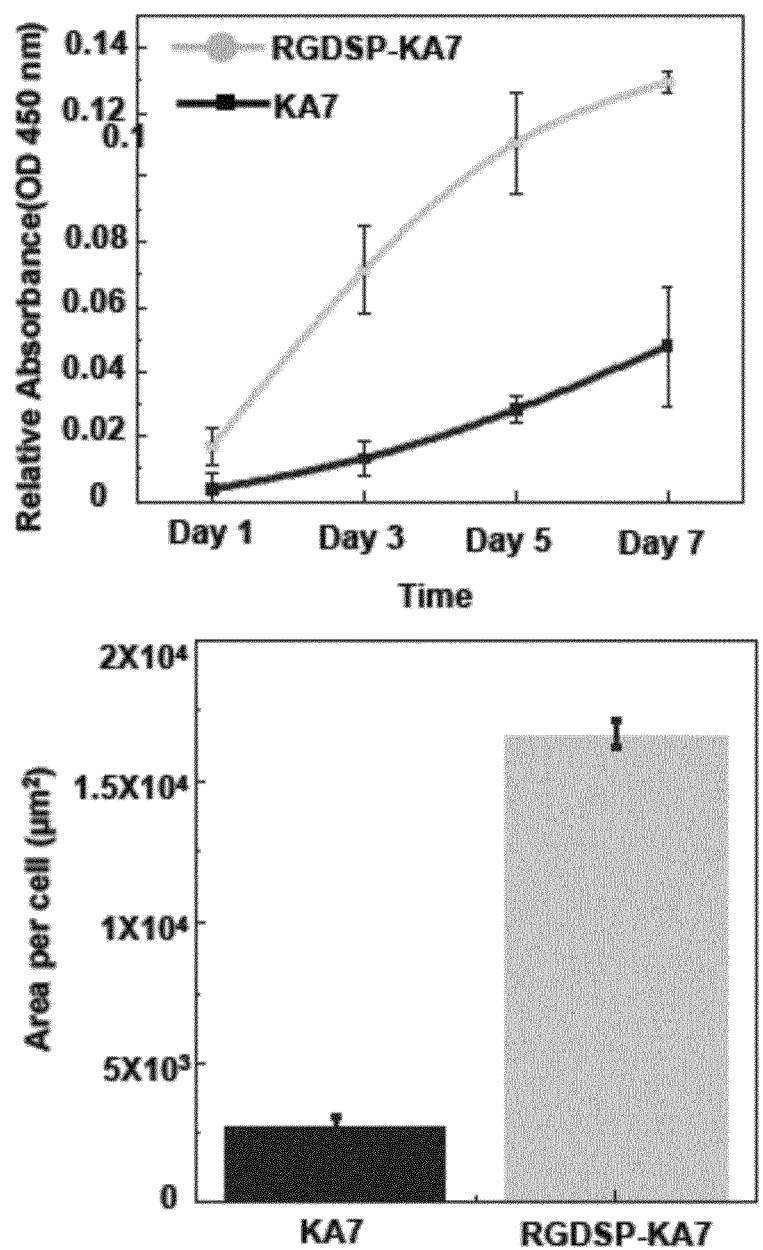
FIG. 4B shows the statistical analysis indicating that MSC can attach and proliferate better on 5 kD-PEG-CWG-GRGDSP-KA7/PEDOT:PSS hydrogel than on 5 kD-PEG-KA7/PEDOT:PSS hydrogel.

First, culturing cells on the conductive hydrogels was investigated. Fibroblast cells and mesenchymal stromal cells (MSC) have been seeded on 5 kD-PEG-KA7/PEDOT:PSS hydrogel and 5 kD-PEG-L2-KA7/PEDOT:PSS hydrogel. As shown in FIGS. 4A and 4B, the presence of the RGDSP (SEQ ID NO: 25) peptide, which is contained in L2, improves the cell adhesion remarkably.

Encapsulating Cells into Conductive Hydrogels

Figure 4C:
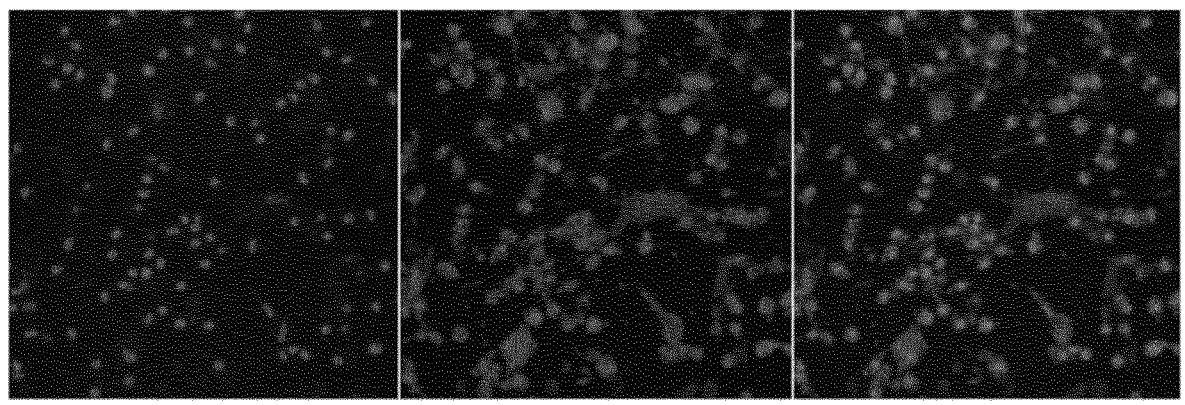
FIG. 4C shows MSCs encapsulated in 5 kD-PEG-KA7/PEDOT:PSS hydrogel.
Figure 4D:
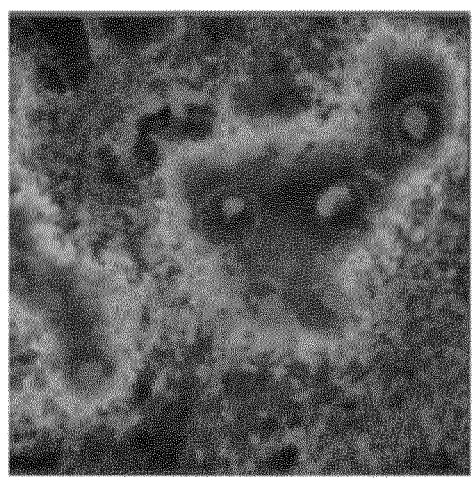
FIG. 4D shows MSCs encapsulated in fluorescently labeled 5 kD-PEG-KA7/PEDOT:PSS hydrogel (in green).
Figure 4E:
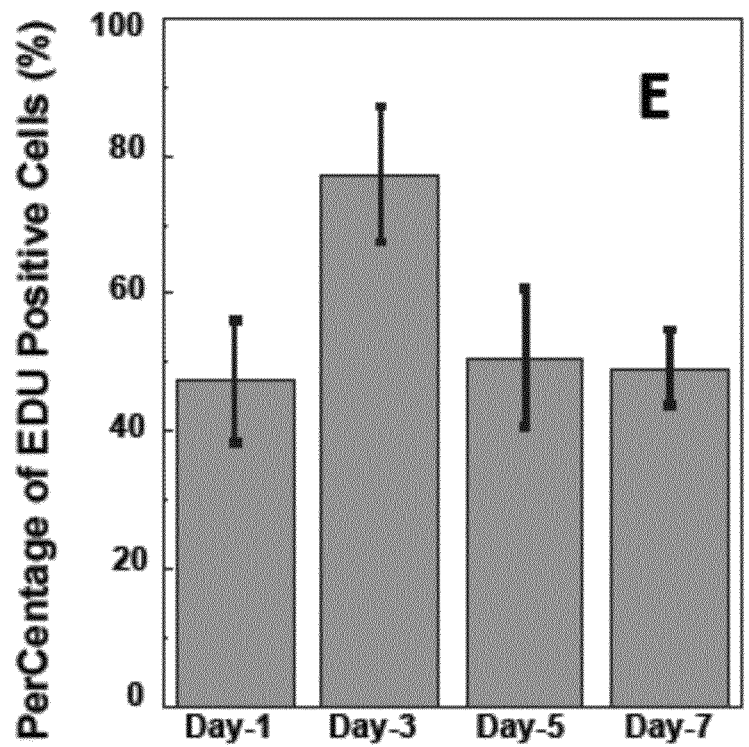
FIG. 4E shows that MSCs encapsulated in 5 kD-PEG-KA7/PEDOT:PSS hydrogel are proliferating, which can be visualized through EdU staining.
Figures 4F, 4G, 4H, 4I:
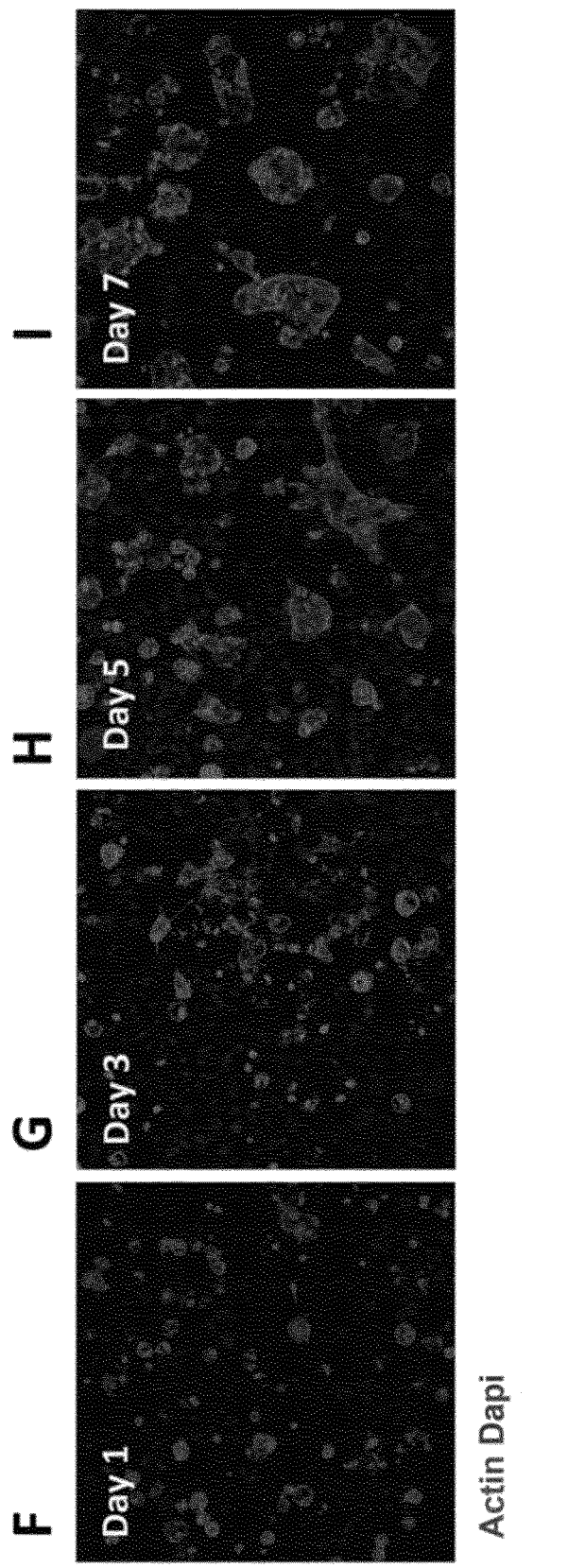
FIG. 4F-I shows that mesenspheres are formed gradually when MSCs are encapsulated in 5 kD-PEG-KA7/PEDOT:PSS hydrogel.

Second, encapsulating cells into conductive hydrogels was investigated. Because the gelation process is free of any organic or electrochemical reaction, cells could be easily encapsulated into the matrix through a simple mixing procedure. MSC or fibroblast was premixed with PEDOT:PSS in cell culture media and added to 5 kD-PEG-KA7 or 5 kD-PEG-L2-KA7 in media. Cells could be observed to disperse evenly in the 3D matrices. Remarkably, cells grew better in 5 kD-PEG-KA7/PEDOT:PSS hydrogel of final concentrations of 500 µM and 1% respectively (0.5 mM/1% hydrogel), as compared to 1 mM/2% hydrogel and 2 mM/2% hydrogels. It is important to note that the 0.5 mM/1% hydrogel is relatively more transparent than the 1 mM/2% and 2 mM/2% hydrogels. This makes it possible to image cells in the dark matrix using light and fluorescence microscopes, while strong light absorption is an intrinsic property of such conductive large aromatic systems. The thymidine analog 5-ethynyl-2'-deoxyuridine (EdU) was used for detection of cell proliferation. While EdU stained MSC were not observed in hydrogel 2 hours after cell encapsulation, a large part of cells in hydrogel incorporated EdU after 6 and 24 hours (FIG. 4C-E). Interestingly, different from culturing MSC on conductive hydrogel, cells grew into sphere-like structures after 5 days in the conductive hydrogel (FIG. 4F-I). The spheres possess a size-distribution similar to the mesenspheres cultured using neural crest and pericyte culture condition with Nestin$^+$ cells, with colony spheres up to 100 µm. Surprisingly, also different from 2D culture, 5 kD-PEG-L2-KA7/PEDOT:PSS hydrogel is less favorable for cell growth and sphere formation, as compared with the 5 kD-PEG-KA7/PEDOT:PSS hydrogel. Given that it is difficult to characterize cells in hydrogels, it was focused on the effect of electrical stimulation (ES) on the morphological changes of MSC.

Differentiation of MSCs to Cardiomyocytes

Figure 4J:
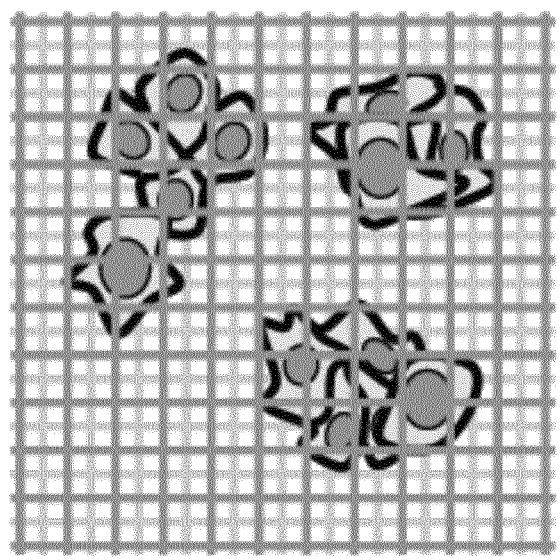
FIG. 4J-K shows applying electric stimulation to MSC after they are encapsulated into 5 kD-PEG-KA7/PEDOT:PSS hydrogel.
Figure 4K:
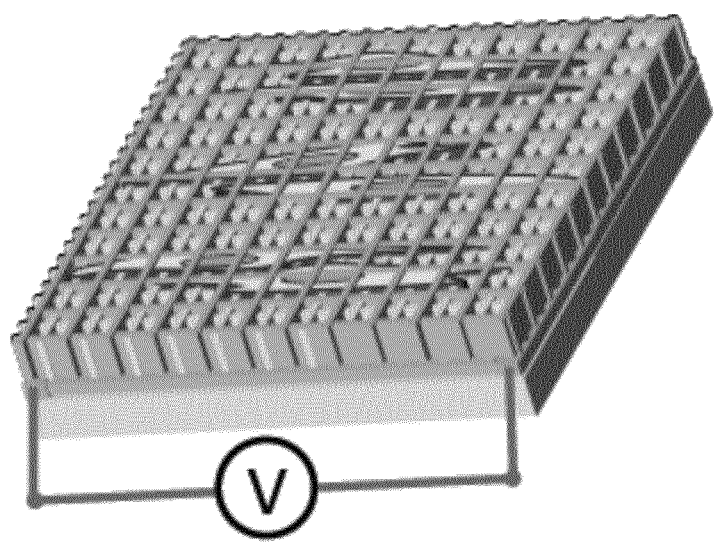
Figure 4L:
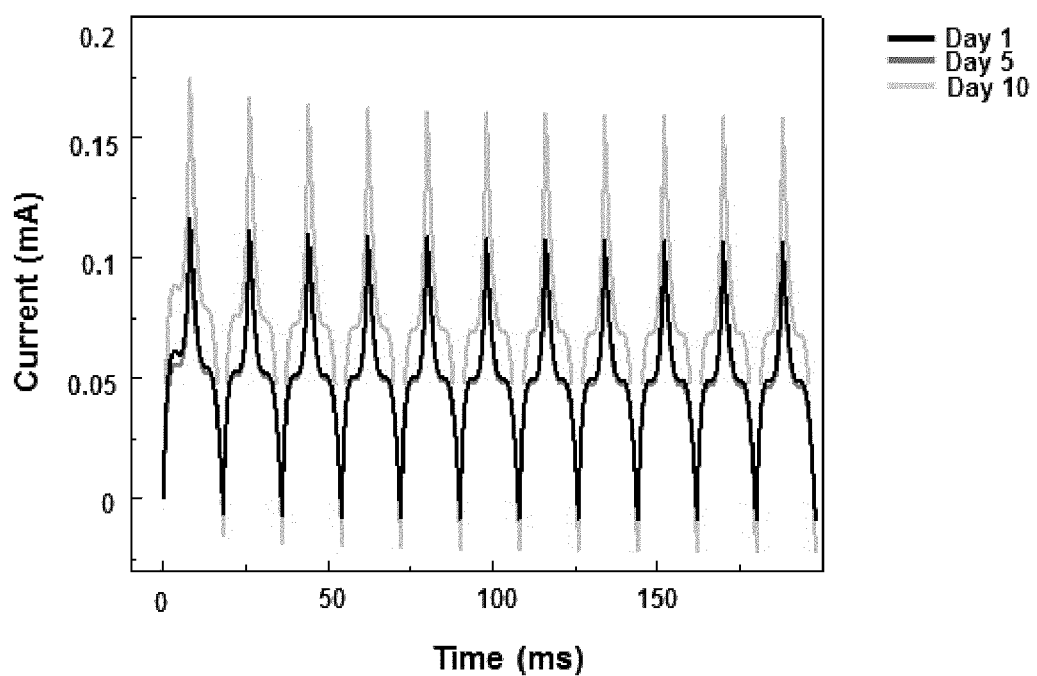
FIG. 4L shows that the electric response of conductive hydrogel changes overtime upon the growth of MSC encapsulated in the 5 kD-PEG-KA7/PEDOT:PSS hydrogel.
Figures 4M, 4N, 4O, 4P:
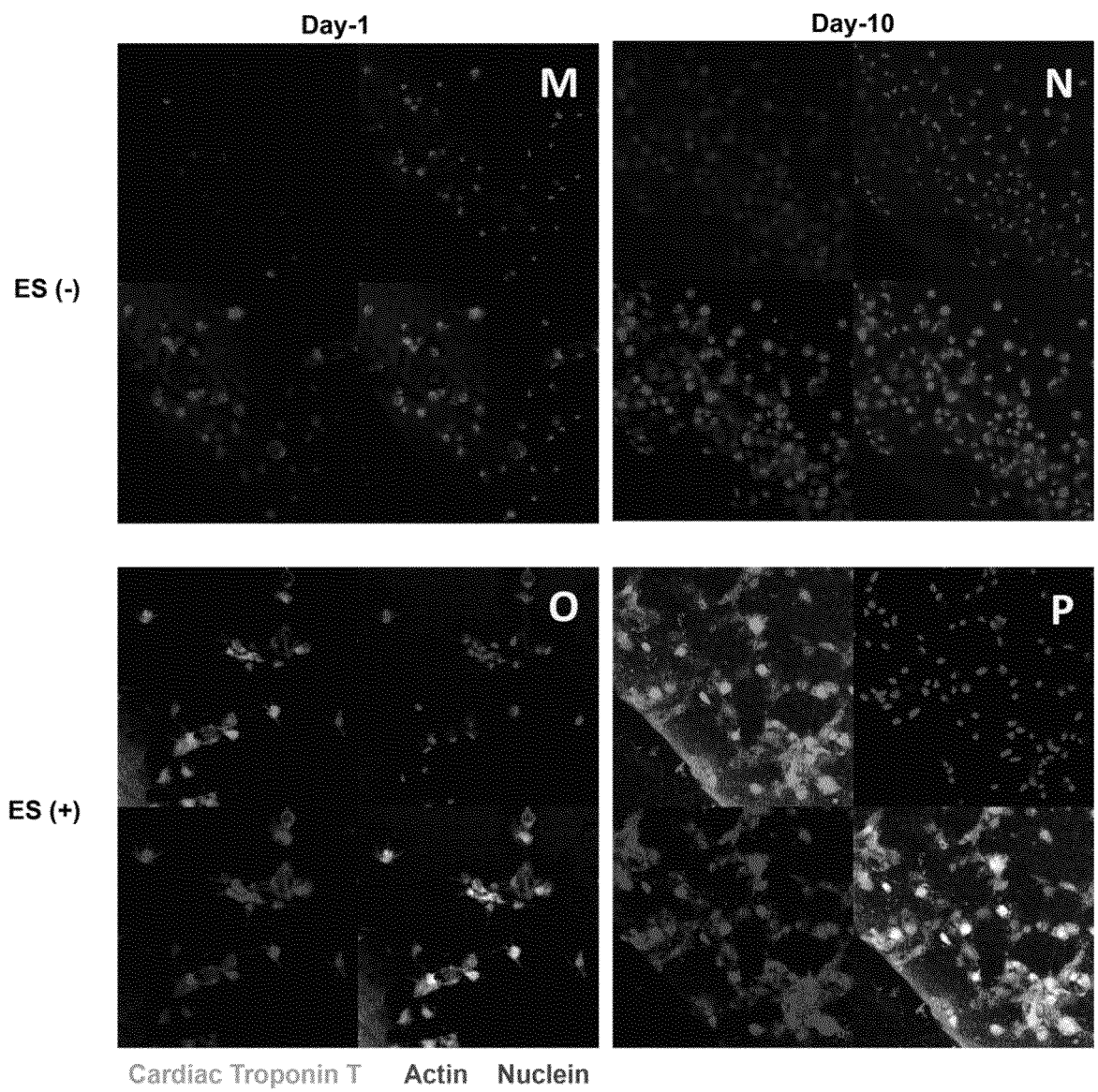

Third, the differentiation of MSCs to cardiomyocytes under ES conditions was investigated. MSC premixed with PEDOT:PSS in culture media was added to 5 kD-PEG-KA7 in media on indium tin oxide (ITO) coated glass slide (FIG. 4J, 4K). The cell-laden hydrogels were then subjected to ES over a time period of 10 days through applying short pulses (2 ms of 500 mV followed by 4 ms interval) for 8 hours in each day. From day 5, cells started to exhibit striated muscle cell phenotype when ES was applied. In the absence of ES, the cells started to form sphere-like structures. Interestingly, there was minor change of conductivity of the sandwiched film during the first 6 days (FIG. 4L), while the measured current increased gradually after day 7, coincident with the gradual formation of striated cardiomyocyte phenotype. This result indicated that the non-covalently assembled conductive matrix could not only provide a seamless cell-materials interface for applying ES to cells in 3D, but also be responsive to the changes in biological environment around cells. As shown in FIG. 4M-P, in addition to the gradual change in morphology, the ES-treated MSCs also exhibited remarkable up-regulation of the myocardiocyte marker cardiac troponin T (cTnT). MSCs in hydrogels were fixed 1 and 10 days after encapsulation and probed by an anti-cTnT antibody. Interestingly, one day after encapsulation, although the morphology of ES-treated cells cannot be distinguished from the control, cTnT expression was observed only on ES-treated cells. After 10 days of culture under ES condition, the cells exhibited high expression of cTnT, while the non-ES-treated cells remained cTnT negative. Upon encapsulation in the conductive 3D matrix, MSCs develop into mesensphere-like structures, whereas ES drives the cells to differentiate into myocardiocyte-like cells.

In summary, the invention provides a modular system to generate conductive hydrogels through a non-covalent assembling approach, aiming to combine the ECM-mimicking hydrogel with organic electronics. While both the mechanical and electronic properties can be tuned by altering the modular structures, the reversibly connected network has also shown self-healing properties. The mobility of electrons in 3D network is affected by the arrangement of the PEDOT, e.g. through $\pi$-$\pi$ inter-chain stacking. As chemically defined biomimetics that does not contain any protein product from biological source, the materials will cause neither server autoimmune response nor batch-to-batch difference in manufacture processes. The crosslinking condition through peptide/PEDOT:PSS interaction avoids organic or electrochemical reaction, while the resulting hydrogels resemble many features of the ECM-mimicking oligosaccharide/starPEG-peptide matrix system and can display bioactive ligands.

These features lead to not only easy cell-encapsulation but also a seamless cell-material interface, which allows to apply ES to cells through the 3D matrix. Interestingly, MSCs form mesensphere-like structures in a 5 kD-PEG-KA7/PEDOT:PSS hydrogel, while upon addition of ES, the cells differentiate into myocardiocyte-like cells.

Example 11: Non-Covalently Assembled Graphene Hydrogel: Modular Structural Motif, Dynamic Self-Healing Network, and Drug Release Hydrogel Formation with Graphene Oxide To test whether the non-covalent assembling approach can also be applied to other conductive polymers, the hydrogel formation using PEG-peptide or starPEG-peptide with graphene derivatives was investigated. While graphene has very poor water solubility, graphene oxide (GO) was used. GO possesses negatively charged carboxylic acid groups and is water-soluble, while electron mobility in the conjugate system is remarkably reduced. After incubation over night with either 5 kD-PEG-KA7 or starPEG-KA7, no hydrogel formation could be observed. Apparently, the carboxylic acid presented on graphene is not sufficient to form stable crosslinking with positively charged peptide-polymer.

Hydrogel Formation with rGO:PSS and rGO:PEDOT:PSS

Reducing GO in the present of PEDOT/PSS leads to rGO/PEDOT:PSS with retained water-solubility, while the conductivity is remarkably enhanced, as compared with GO. Reducing GO in the present of PSS also led to water-soluble and conductive material rGO/PSS. Hydrogel formation using rGO:PSS or rGO:PEDOT:PSS (FIG. 5A) was tested. Mixing rGO/PEDOT:PSS with starPEG-KA7 to final concentrations of 0.5% and 2 mM respectively led to homogeneously formed hydrogels. The rGO:PEDOT:PSS/starPEG-KA7 hydrogel is mechanically more robust than the rGO:PSS/starPEG-KA7 hydrogel. The rGO:PEDOT:PSS/starPEG-KA7 hydrogel has shown a storage modulus of 2000 Pa, while the storage modulus of the rGO:PSS/starPEG-KA7 hydrogel is below 100 Pa. When KA7 peptide is connected to 5 k linear PEG, mixing 5 kD-PEG-KA7 and rGO:PEDOT:PSS led to very soft hydrogel (<100 Pa).

Drug Release with StarPEG-KA7/rGO:PEDOT:PSS and 5kD-PEG-KA7/PEDOT:PSS

Because the networks of PEG-peptide/PEDOT:PSS hydrogel and the PEG-peptide/rGO:PEDOT:PSS hydrogels are amphipathic, they can bind to both hydrophobic and charged hydrophilic compounds. The encapsulation of hydrophilic and hydrophobic drug compounds was tested. PEDOT:PSS was premixed with either hydrophilic compound doxorubicin or hydrophobic compound paclitaxel, followed by adding 5 kD-PEG-KA7. The presence of drug compounds did not disturb the gelation. Doxorubicin can be encapsulated with a concentration of 0.8 mg/mL, while 0.1 mg/mL paclitaxel can be encapsulated into the hydrogel. Paclitaxel in excess formed precipitate at the bottom. rGO:PEDOT:PSS was premixed with either doxorubicin or paclitaxel, followed by adding starPEG-KA7. The presence of drug compounds did not disturb the gelation. Doxorubicin can be encapsulated with a concentration as high as 0.8 mg/mL, while 1.0 mg/mL paclitaxel can be encapsulated into the hydrogel. The hydrogels loaded with drugs were then incubated in PBS, and the release of drugs was monitored. The release of paclitaxel from starPEG-KA7/rGO:PEDOT:PSS is similar to that from 5 kD-PEG-KA7/PEDOT:PSS.

Self-Healing Dynamic Network

To demonstrate the self-healing property of the dynamic network, a step-strain rheological measurement using the starPEG-KA7/rGO:PEDOT:PSS hydrogel was performed. After forming a hydrogel by mixing 1.0 mM starPEG-KA7 and 1% rGO:PEDOT:PSS, strong strain was applied to break the hydrogel and the recovery of storage modulus was followed. As shown in FIG. 5B, instant recovery of the hydrogel characteristic (G'>>G") was observed after the applied strain was removed. Full recovery of stiffness occurred after about 20 min.

Interestingly, as compared with the 5 kD-PEG-KA7/PEDOT:PSS hydrogel (storage modulus 1000 Pa), starPEG-KA7/rGO:PEDOT:PSS hydrogel is stiffer, with a storage modulus of 3000 Pa. However, the yield stress for starPEG-KA7/rGO:PEDOT:PSS hydrogel is 5-time lower than that of 5 kD-PEG-KA7/PEDOT:PSS hydrogel. This rheological observation has also been confirmed by probing the material by manual perturbation. Pipetting the 5 kD-PEG-KA7/PEDOT:PSS hydrogel vigorously could easily break the hydrogel into small pieces. However, the small pieces can self-heal to form an intact piece of hydrogel after incubating overnight. After breaking starPEG-KA7/rGO:PEDOT:PSS hydrogel, the materials can also self-heal, though significantly slower than the 5 kD-PEG-KA7/PEDOT:PSS hydrogel.

Thermal Therapy and Release

PEDOT:PSS and rGO:PEDOT:PSS have the maximal absorption in the near IR region (FIG. 6A8A), of which most tissues have the minimal absorption. It can be used in thermal therapy with IR light (FIG. 8B). Heat can also cause release of pre-loaded drug from the matrix (FIG. 8C), to achieve spatiotemporal control of pharmacological effect through using or combining light and/or electric current.

---

The invention claimed is:

1. A conductive hydrogel comprising
poly(3,4-ethylenedioxythiophene) polystyrene sulfonate (PEDOT:PSS) and
a conjugate of a linker-(BX)n oligopeptide and polyethylene glycol (PEG) according to formula (I):

PEG-linker-(BX)n    (I)

wherein
(BX)n is KA7 (SEQ ID NO: 3) and
the linker is L2 (SEQ ID NO: 14).

2. The conductive hydrogel according to claim 1, wherein said conductive hydrogel further comprises at least one sulfated oligosaccharide selected from the group consisting of heparin, heparan sulfate, chondroitin sulfate, dermatan sulfate, keratin sulfate, dextran sulfate, α-cyclodextrin sulfate, β-cyclodextrin sulfate, γ-cyclodextrin sulfate, α-cyclodextrin phosphate, β-cyclodextrin phosphate and γ-cyclodextrin phosphate.

3. The conductive hydrogel according to claim 1, wherein said conductive hydrogel is assembled non-covalently.

4. The conductive hydrogel according to claim 1, wherein said PEG is a linear PEG or a starPEG.

5. The conductive hydrogel according to claim 4, wherein said
starPEG is a 4-arm star PEG with a molecular weight in the range of 4 kD to 40 kD
or
wherein said linear PEG has a molecular weight in the range of 1 kD to 100 kD.

6. The conductive hydrogel according to claim 1, wherein said PEG is maleimide-functionalized, carboxylic acid-functionalized, amino-functionalized, azide-functionalized, or alkyne-functionalized.

7. The conductive hydrogel according to claim 3, wherein the conjugate is 5kD-PEG-L2-KA7, 10kD-PEG-L2-KA7, or 20kD-PEG-L2-KA7.

8. The conductive hydrogel according to claim 1, further comprising cells, organoids, a morphogen or at least one active pharmaceutical ingredient.

9. The conductive hydrogel according to claim 8, wherein
said cells are selected from fibroblast cells, mesenchymal stromal cells (MSC), neuronal progenitor cells (NPC), human umbilical vein endothelial cells (HUVEC);
said at least one pharmaceutical active ingredient is selected from doxorubicin, paclitaxel, cyclosporin A, tacrolimus, rapamycin, anti-VEGF antibody, anti-TNF-α antibody; or
said morphogen is selected from TNF-α, TGF-β, IFN-γ, FGF, VEGF, and EGF.

10. A process for preparing a conductive hydrogel according to claim 1, said process comprising the steps of
i) preparing a conjugate of polyethylene glycol (PEG) and a linker-(BX)n oligopeptide of formula (I):

PEG-linker-(BX)n     (I), wherein (BX)n is KA7 (SEQ ID NO: 3) and the linker is L2 (SEQ ID NO: 14);
ii) mixing said conjugate of polyethylene glycol (PEG) and oligopeptide of formula (I) with PEDOT:PSS;
iii) forming the conductive hydrogel by gelation.

11. A process for preparing a conductive hydrogel matrix comprising cells or organoids, said process comprising the steps of
i) preparing a conjugate of polyethylene glycol (PEG) and a linker-(BX)n oligopeptide of formula (I):

PEG-linker-(BX)n     (I), wherein (BX)n is KA7 (SEQ ID NO: 3) and the linker is L2 (SEQ ID NO: 14);
ii) premixing cells or organoids with PEDOT:PSS in a culture medium;
iii) mixing said conjugate of polyethylene glycol (PEG) and oligopeptide of formula (I) with the culture medium comprising the cells or organoids premixed with PEDOT:PSS; and
iv) forming the conductive hydrogel matrix by gelation to encapsulate the cells or organoids into the hydrogel matrix.

12. A process for preparing a conductive hydrogel matrix comprising a morphogen or an active pharmaceutical ingredient, said process comprising the steps of
i) preparing a conjugate of polyethylene glycol (PEG) and a linker-(BX)n oligopeptide of formula (I):

PEG-linker-(BX)n     (I), wherein (BX)n is KA7 (SEQ ID NO: 3) and the linker is L2 (SEQ ID NO: 14);
ii) premixing an active pharmaceutical ingredient or morphogen with PEDOT:PSS in a solution
iii) mixing said conjugate of polyethylene glycol (PEG) and oligopeptide of formula (I) of step i) with the solution of step ii) comprising the premixed active pharmaceutical ingredient or morphogen and PEDOT:PSS;
iv) forming the conductive hydrogel matrix by gelation.

13. A process for preparing a conductive hydrogel matrix comprising cells or organoids, said process comprising the steps of
i) preparing a conjugate of polyethylene glycol (PEG) and a linker-(BX)n oligopeptide of formula (I):

PEG-linker-(BX)n     (I), wherein (BX)n is KA7 (SEQ ID NO: 3) and the linker is L2 (SEQ ID NO: 14);
ii) mixing said conjugate of polyethylene glycol (PEG) and oligopeptide of formula (I) with PEDOT:PSS;
iii) forming the conductive hydrogel matrix by gelation;
iv) seeding cells or organoids onto the hydrogel matrix obtained by step iii) as described above; and
v) incubating said hydrogel matrix and said seeded cells or organoids to facilitate cell adhesion to the conductive hydrogel matrix.

* * * * *